(12) United States Patent
Dewey

(10) Patent No.: US 10,076,421 B2
(45) Date of Patent: *Sep. 18, 2018

(54) EXPANDABLE IMPLANT AND INSERTION TOOL

(71) Applicant: Warsaw Orthopedic, Inc., Warsaw, IN (US)

(72) Inventor: Jonathan M. Dewey, Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/824,253

(22) Filed: Nov. 28, 2017

(65) Prior Publication Data

US 2018/0078385 A1 Mar. 22, 2018

Related U.S. Application Data

(63) Continuation of application No. 15/008,805, filed on Jan. 28, 2016.

(51) Int. Cl.
*A61F 2/44* (2006.01)
*A61F 2/46* (2006.01)

(52) U.S. Cl.
CPC .......... *A61F 2/4455* (2013.01); *A61F 2/4611* (2013.01); *A61F 2002/4475* (2013.01); *A61F 2220/0041* (2013.01)

(58) Field of Classification Search
CPC combination set(s) only.
See application file for complete search history.

(56) References Cited

U.S. PATENT DOCUMENTS

| 7,850,733 | B2 | 12/2010 | Baynham et al. |
| 7,875,078 | B2 | 1/2011 | Wysocki et al. |
| 7,909,869 | B2 | 3/2011 | Gordon et al. |
| 8,062,375 | B2 | 11/2011 | Glerum et al. |
| 8,105,358 | B2 | 1/2012 | Phan |
| 8,105,382 | B2 | 1/2012 | Olmos et al. |
| 8,123,810 | B2 | 2/2012 | Gordon et al. |
| 8,133,232 | B2 | 3/2012 | Levy et al. |
| 8,187,332 | B2 | 5/2012 | Mcluen |
| 8,382,842 | B2 | 2/2013 | Greenhalgh et al. |
| 8,394,145 | B2 | 3/2013 | Weiman |
| 8,398,713 | B2 | 3/2013 | Weiman |
| 8,403,990 | B2 | 3/2013 | Dryer et al. |
| 8,435,298 | B2 | 5/2013 | Weiman |
| 8,491,659 | B2 | 7/2013 | Weiman |
| 8,518,120 | B2 | 8/2013 | Glerurn et al. |
| 8,523,944 | B2 | 9/2013 | Jimenez et al. |

(Continued)

OTHER PUBLICATIONS

International Search Report dated May 12, 2017 from International Application No. PCT/US2017/015356.

*Primary Examiner* — Jan Christopher Merene

(57) ABSTRACT

An expandable implant includes a body portion, a carriage portion, a deployment assembly, and an expandable portion. The deployment assembly and the expandable portion are attached to the carriage portion, and portions of the carriage portion are moveable out of and into the body portion. When the expandable implant is inserted into a disc space, the expandable portion is expandable to push the upper vertebral body and the lower vertebral body away from one another.

20 Claims, 16 Drawing Sheets

(56) References Cited

U.S. PATENT DOCUMENTS

| | | |
|---|---|---|
| 8,556,979 B2 | 10/2013 | Weiman et al. |
| 8,568,481 B2 | 10/2013 | Olmos |
| 8,628,577 B1 | 1/2014 | Jimenez |
| 8,628,578 B2 | 1/2014 | Miller et al. |
| 8,632,595 B2 | 1/2014 | Weiman |
| 8,663,329 B2 | 3/2014 | Ernst |
| 8,679,183 B2 | 3/2014 | Glerurn et al. |
| 8,685,098 B2 | 4/2014 | Glerum et al. |
| 8,709,086 B2 | 4/2014 | Glerum et al. |
| 8,778,025 B2 | 7/2014 | Ragab et al. |
| 8,795,366 B2 | 8/2014 | Varela |
| 8,888,853 B2 | 11/2014 | Glerum et al. |
| 8,888,854 B2 | 11/2014 | Glerurn et al. |
| 8,894,711 B2 | 11/2014 | Varela |
| 8,894,712 B2 | 11/2014 | Varela |
| 8,926,704 B2 | 1/2015 | Glerurn |
| 8,940,049 B1 | 1/2015 | Jimenez |
| 9,039,771 B2 | 5/2015 | Glerum et al. |
| 9,119,730 B2 | 9/2015 | Glerum et al. |
| 9,522,070 B2 * | 12/2016 | Flower .................... A61F 2/447 |
| 9,603,717 B2 | 3/2017 | Ibarra |
| 2004/0087947 A1 * | 5/2004 | Lim ...................... A61F 2/4465 606/247 |
| 2005/0143749 A1 | 6/2005 | Zalenski et al. |
| 2009/0222100 A1 | 9/2009 | Cipoletti |
| 2010/0076491 A1 | 3/2010 | Glenn et al. |
| 2011/0054621 A1 | 3/2011 | Lim |
| 2011/0172721 A1 | 7/2011 | Varela |
| 2011/0172774 A1 | 7/2011 | Varela |
| 2012/0035729 A1 | 2/2012 | Glerum et al. |
| 2012/0109319 A1 | 5/2012 | Perisic |
| 2012/0150304 A1 | 6/2012 | Glerum et al. |
| 2012/0150305 A1 | 6/2012 | Glerum et al. |
| 2012/0158146 A1 | 6/2012 | Glerum et al. |
| 2012/0158147 A1 | 6/2012 | Glerum et al. |
| 2012/0158148 A1 | 6/2012 | Glerum et al. |
| 2013/0144388 A1 | 6/2013 | Emery et al. |
| 2013/0158664 A1 | 6/2013 | Palmatier et al. |
| 2014/0121774 A1 | 5/2014 | Glerum et al. |
| 2014/0156006 A1 | 6/2014 | Bannigan et al. |
| 2014/0277471 A1 | 9/2014 | Gray et al. |
| 2014/0324171 A1 | 10/2014 | Glerum et al. |
| 2014/0343678 A1 | 11/2014 | Suddaby |
| 2015/0018954 A1 | 1/2015 | Loebl et al. |
| 2016/0331544 A1 | 11/2016 | Braddock, Jr. |
| 2017/0056197 A1 | 3/2017 | Weiman |
| 2017/0216045 A1 * | 8/2017 | Dewey .................... A61F 2/447 |
| 2017/0333198 A1 * | 11/2017 | Robinson ................ A61F 2/447 |

* cited by examiner

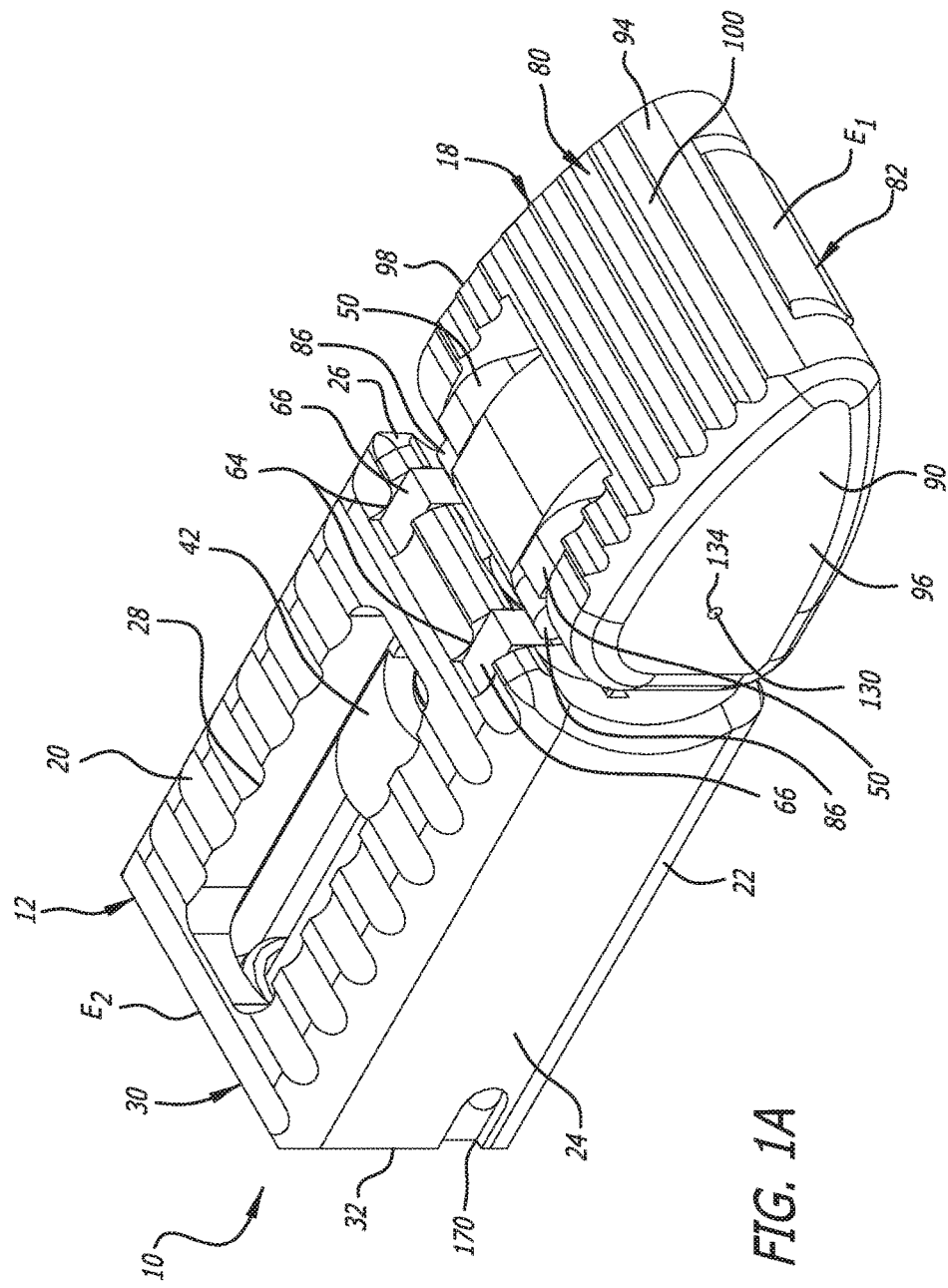

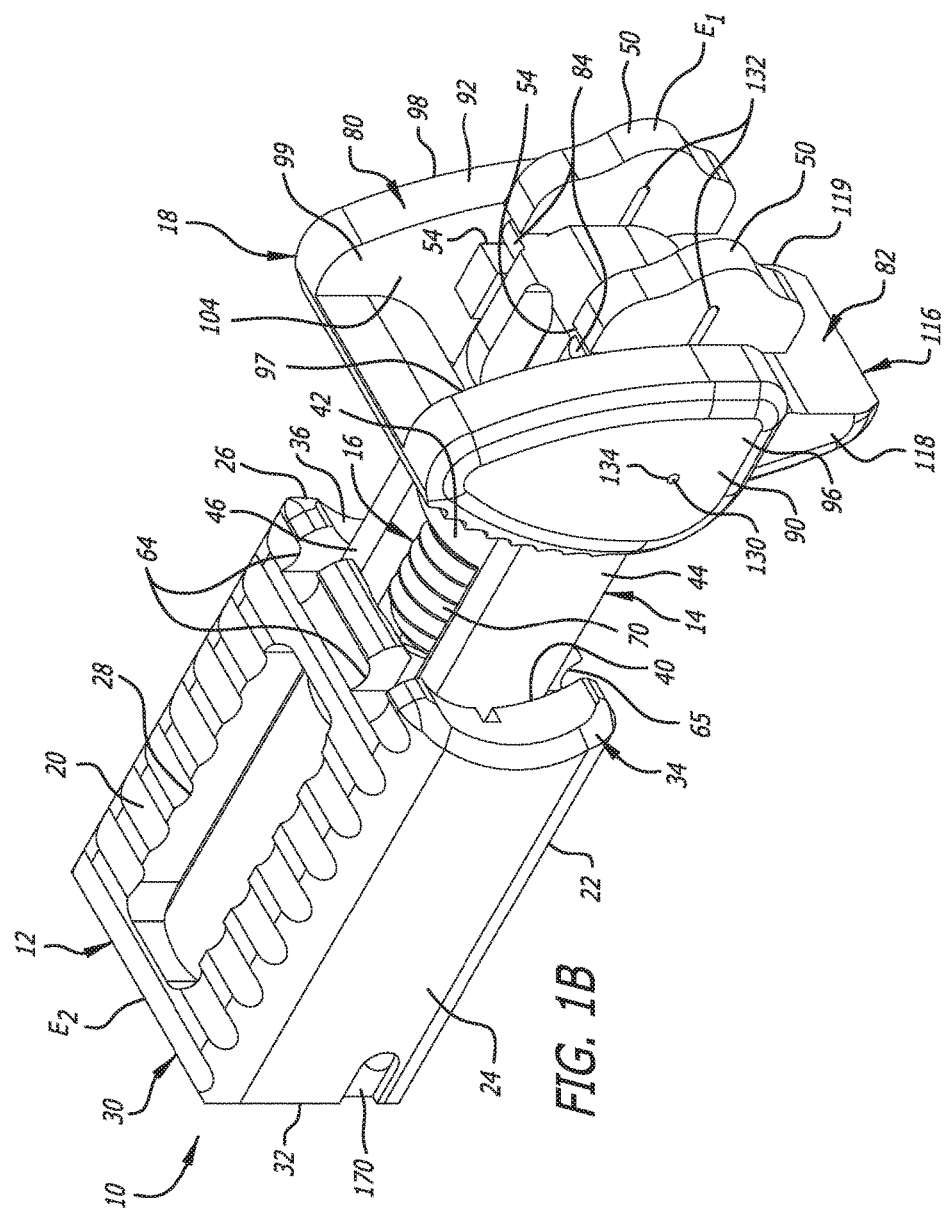

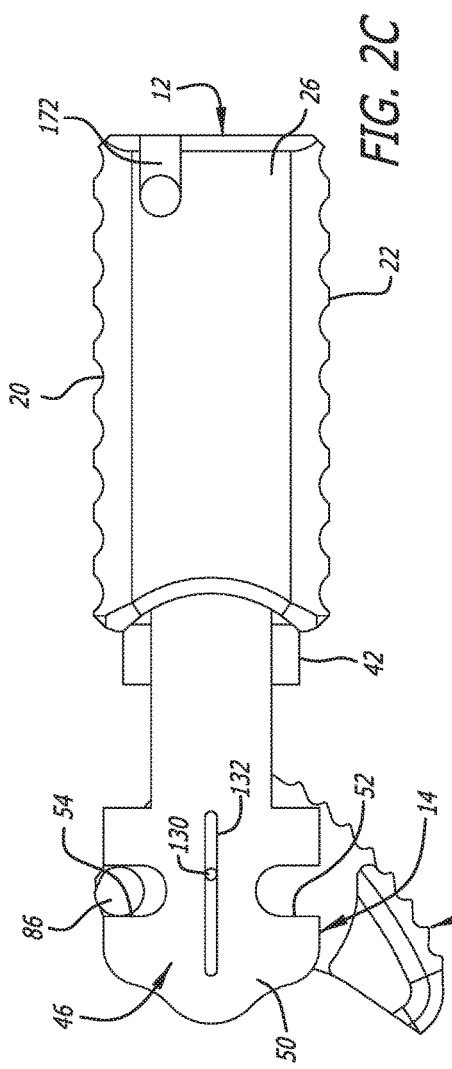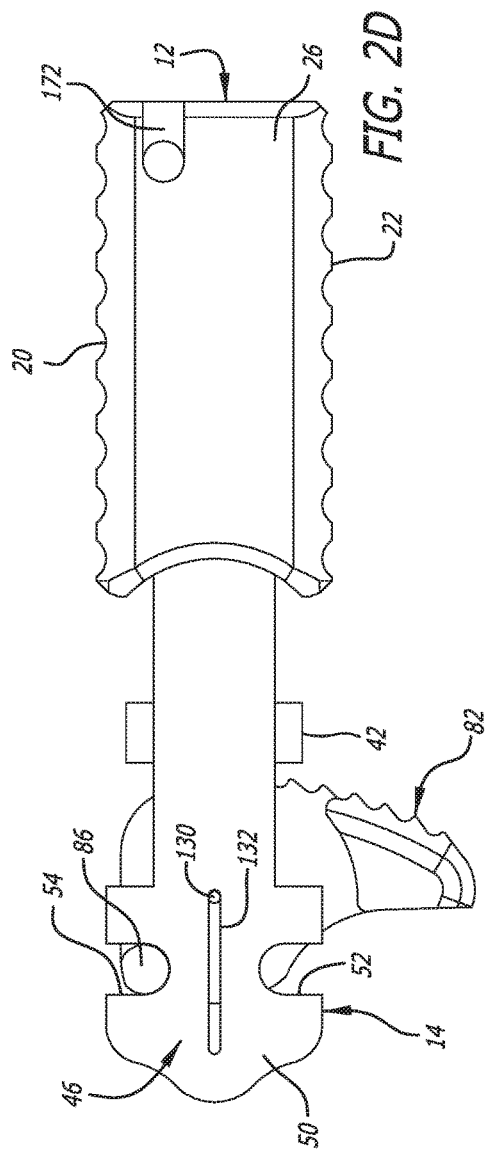

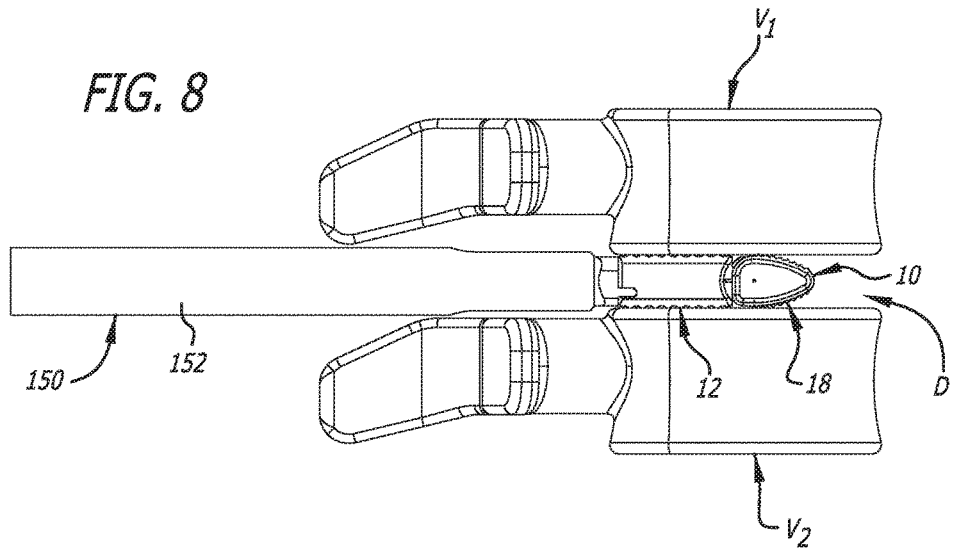
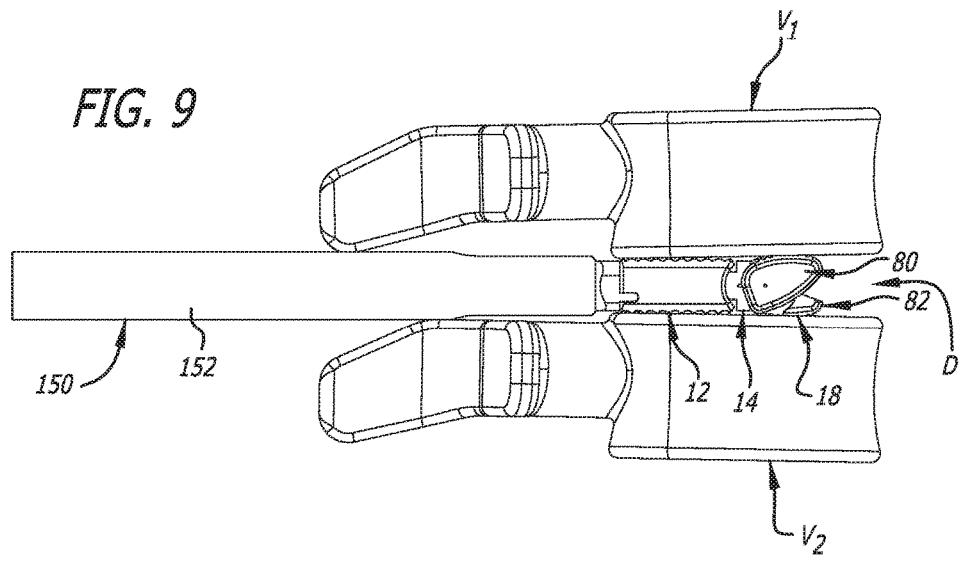

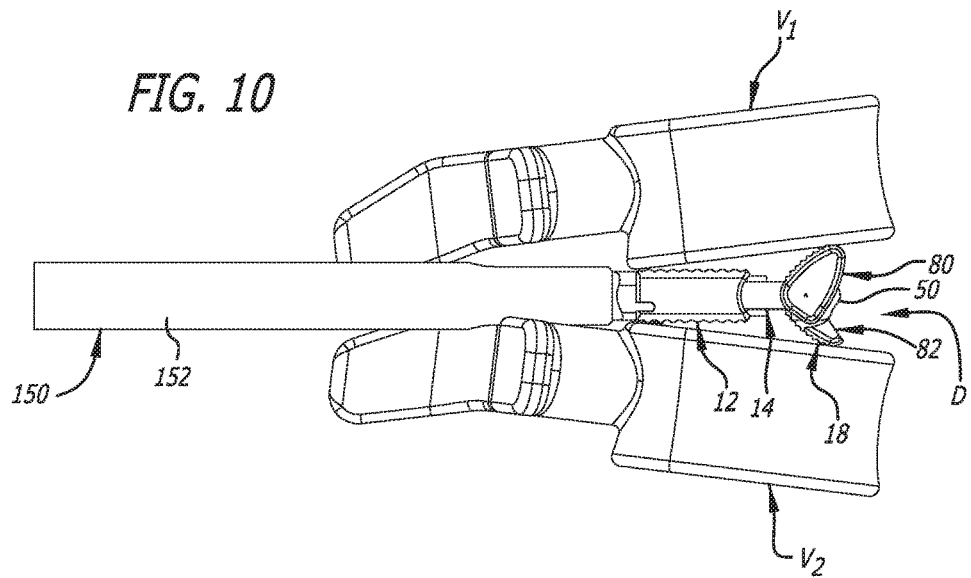
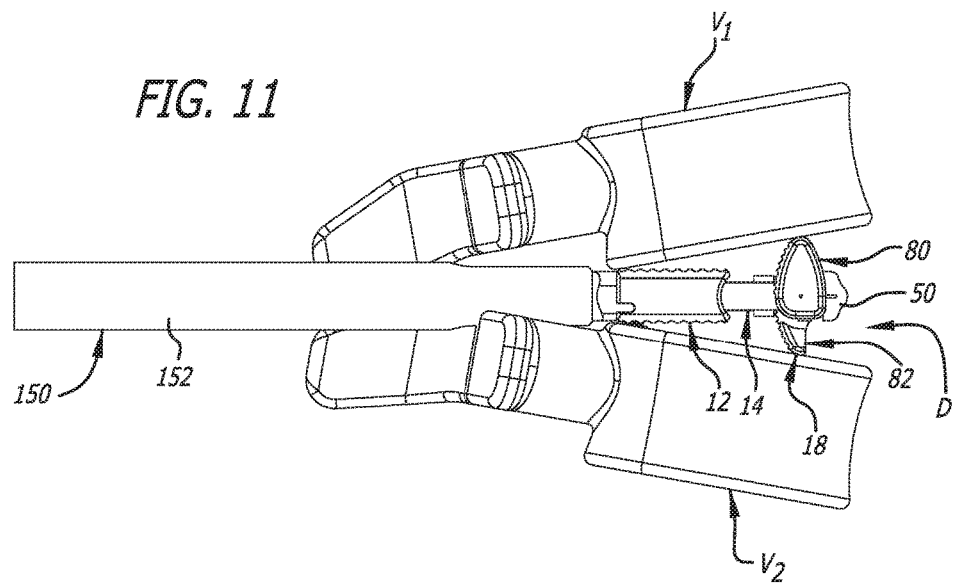

EXPANDABLE IMPLANT AND INSERTION TOOL

The present application is a continuation of U.S. application Ser. No. 15/008,805, filed Jan. 28, 2016; all of which is incorporated herein by reference.

BACKGROUND OF THE INVENTION

Field of the Invention

The present invention relates to an expandable implant for insertion in a disc space used to move adjacent vertebral bodies apart from one another. More specifically, the present invention relates to an expandable implant and an insertion instrument used in actuating the expandable implant to at the very least open and close an upper jaw portion and a lower jaw portion. More particularly, the present invention relates to expandable implant including an upper jaw portion, a lower jaw portion, and a carriage portion carrying the upper jaw portion and the lower jaw portion, and an insertion instrument used to facilitate opening and closing of the upper jaw portion and the lower jaw portion, and to facilitate movement of the carriage portion.

Description of the Prior Art

Some of the degenerative conditions that affect the spine of a patient may be so severe as to require surgical intervention. Oftentimes, the degenerative conditions are such that a spinal implant is required to restore or enhance spinal lordosis. Such spinal implants are insertable into a disc space between two adjacent vertebral bodies of adjacent vertebrae of the patient. Lordotic, frusto-conical, or tapered, spinal implants have the advantage of aiding in the restoration or enhancement of spinal lordosis.

Push-in spinal implants offer the advantage of being easily positioned in the implantation space and of having excellent fastening or holding features. Expandable implants offer the advantage of allowing for the placement of a potentially larger implant through a smaller opening in the patient's body. However, there is a need for a push-in expandable spinal implant that at the very least includes a mechanism for increasing the length of the spinal implant after implantation thereof in a disc space between two adjacent vertebral bodies.

SUMMARY OF THE INVENTION

The present invention in one preferred embodiment contemplates an expandable spinal implant for insertion in a disc space between adjacent upper and lower vertebral bodies, the expandable spinal implant including a body portion having a trailing end, a leading end, an upper surface for engaging an endplate of the upper vertebral body, a lower surface for engaging an endplate of the lower vertebral body, and an interior cavity being configured to receive at least a portion of a carriage portion; the carriage portion having a first arm portion, a second arm portion, a collar portion spacing apart and attaching the first arm portion and the second arm portion to one another, head portions attached to the first arm portion and the second arm portion, and slots extending along the first arm portion and the second arm portion, portions of the first arm portion and the second arm portion being receivable within the interior cavity of the body portion, and the first arm portion and the second arm portion being moveable between a retracted position and an expanded position relative to the body portion, the collar portion including a threaded aperture extending therethrough, the head portions being configured to support portions of an expandable portion, and the slots being configured to receive a pin for attaching the portions of the expandable portion to the carriage portion; the expandable portion including an upper jaw portion and a lower jaw portion, the upper jaw portion and the lower jaw portion being attached to the head portions of the first arm portion and the second arm portion, the upper jaw portion and the lower portion having apertures therein for receiving the pin therethrough to attach the upper jaw portion and the lower jaw portion to the head portions of the first arm portion and the second arm portion; and a deployment portion including a deployment screw and a yoke portion engaging the deployment screw, at least a portion of the deployment screw being received in the threaded aperture of the collar portion, and the yoke portion including an aperture therein for receiving the pin therethrough to attach the yoke portion to the upper jaw portion, the lower jaw portion, and the head portions of the first arm portion and the second arm portion, the deployment screw being moveable between a first position and a second position via rotation thereof with respect to the threaded aperture of the collar portion, where rotational movement of the deployment screw serves to move the yoke portion and the pin received therethrough along the slots of the carriage portion, and movement of the pin in the slots serves to move the upper jaw portion and the lower jaw portion between a closed position and an open position.

The present invention in another preferred embodiment contemplates an expandable spinal implant for insertion in a disc space between adjacent upper and lower vertebral bodies, the expandable spinal implant including a body portion having an interior cavity being configured to receive at least a portion of a carriage portion; the carriage portion including a threaded aperture therethrough, the carriage portion being moveable between a retracted position and an expanded position relative to the body portion, and the carriage portion including at least one slot therethrough, the carriage portion being configured to support portions of an expandable portion, and the at least one slot being configured to receive a pin for attaching the portions of the expandable portion to the carriage portion; the expandable portion including an upper jaw portion and a lower jaw portion, the upper jaw portion and the lower portion having apertures therein for receiving the pin therethrough to attach the upper jaw portion and the lower jaw portion to the carriage portion; and a deployment portion including a deployment screw and a yoke portion engaging the deployment screw, at least a portion of the deployment screw being received in the threaded aperture of the carriage portion, and the yoke portion including an aperture therein for receiving the pin therethrough to attach the yoke portion to the upper jaw portion, the lower jaw portion, and the carriage portion, the deployment screw being moveable between a first position and a second position via rotation thereof with respect to the threaded aperture of the carriage portion, where rotational movement of the deployment screw serves to move the yoke portion and the pin received therethrough along the at least one slot of the carriage portion, and movement of the pin in the at least one slot serves to move the upper jaw portion and the lower jaw portion between a closed position and an open position.

The present invention in yet another preferred embodiment contemplates a method of inserting an expandable spinal implant into a disc space between two adjacent vertebral bodies using an insertion instrument, the method including providing an expandable spinal implant having a body portion, a carriage portion, a deployment portion, and an expandable portion, the carriage portion being moveable relative to the body portion from a retracted position to an extended position, the carriage portion supporting the expandable portion, the deployment portion being attached to the carriage portion and the expandable portion, the deployment portion being moveable between at least a first position and a second position to facilitate movement of the expandable portion between a closed position and an open position; providing an insertion instrument having a pusher tool and a driver tool, at least a portion of the driver tool being received with the pusher tool, the pusher tool being engageable to the expandable spinal implant to move the carriage portion from the retracted position to the extended position, and the driver tool being engageable to the expandable spinal implant to move the expandable portion from the closed position to the open position; releasably engaging the insertion instrument to the expandable spinal implant; inserting the expandable spinal implant into the disc space between the two adjacent vertebral bodies using the insertion instrument, actuating the pusher tool to move the carriage portion from the retracted position to the extended position; and actuating the driver tool to move the deployment portion from the first position to the second position to move the expandable portion from the closed position to the open position.

These and other objects of the present invention will be apparent from review of the following specification and the accompanying drawings.

BRIEF DESCRIPTION OF THE DRAWINGS

FIG. 1A is a perspective view of a first embodiment of an expandable implant according to the present invention depicting a carriage portion thereof positioned in a retracted position and an expandable portion thereof in a closed position;

FIG. 1B is a perspective view of the expandable implant of FIG. 1A depicting the carriage portion thereof in an extended position and the expandable portion thereof in an open position;

FIG. 2C is a side elevational view of the expandable implant of FIG. 1A with the upper jaw portion removed to show the lower jaw portion in a second intermediate position;

FIG. 2D is a side elevational view of the expandable implant of FIG. 1A with the upper jaw portion removed to show the lower jaw portion in a position corresponding to the open position of the expandable portion;

FIG. 8 is a side elevational view of the expandable implant of FIG. 1A inserted into the disc space by the insertion instrument with the carriage portion in the retracted position and the expandable portion thereof in the closed position;

FIG. 9 is a side elevational view of the expandable implant of FIG. 1A inserted into the disc space by the insertion instrument with the carriage portion in a first partially extended position and the expandable portion in a first partially open position;

FIG. 10 is a side elevational view of the expandable implant of FIG. 1A inserted into the disc space by the insertion instrument with the carriage portion in a second partially extended position and the expandable portion in a second partially open position;

FIG. 11 is a side elevational view of the expandable implant of FIG. 1A inserted into the disc space by the insertion instrument with the carriage portion in the extended position and the expandable portion in the open position;

DETAILED DESCRIPTION OF THE PREFERRED EMBODIMENT

In accordance with one preferred embodiment of the present invention, and as depicted in FIGS. 1A, 1B, 3, and 8-16, an expandable interbody spinal implant is generally indicated by the numeral 10. The expandable implant 10 includes a distal end $E_1$, and a proximal end $E_2$ opposite from one another. The expandable implant 10 is reconfigurable from an unexpanded configuration (FIG. 1A) to an expanded configuration (FIG. 1B). As depicted in FIGS. 1A and 1B, the distal end $E_1$ will change depending on whether the expandable implant 10 is in the unexpanded configuration or the expanded configuration.

As depicted in FIGS. 8-11, the expandable implant 10 is insertable into a disc space D between two adjacent vertebral bodies of a first upper vertebrae $V_1$ and a second lower vertebrae $V_2$. The expandable implant 10 can be inserted anteriorly or posteriorly (FIGS. 8-11). Furthermore, the expandable implant 10 can be configured as a spinal fusion implant to facilitate fusion between the two adjacent vertebral bodies of the vertebrae $V_1$ and $V_2$. As depicted in FIGS. 2A-2D and 8-11, portions of the expandable implant 10 are configured to expand, and such expansion (upon insertion of the implant 10 into disc space D) serves in pushing the two adjacent vertebral bodies of the vertebrae $V_1$ and $V_2$ apart from one another.

Figure 12:
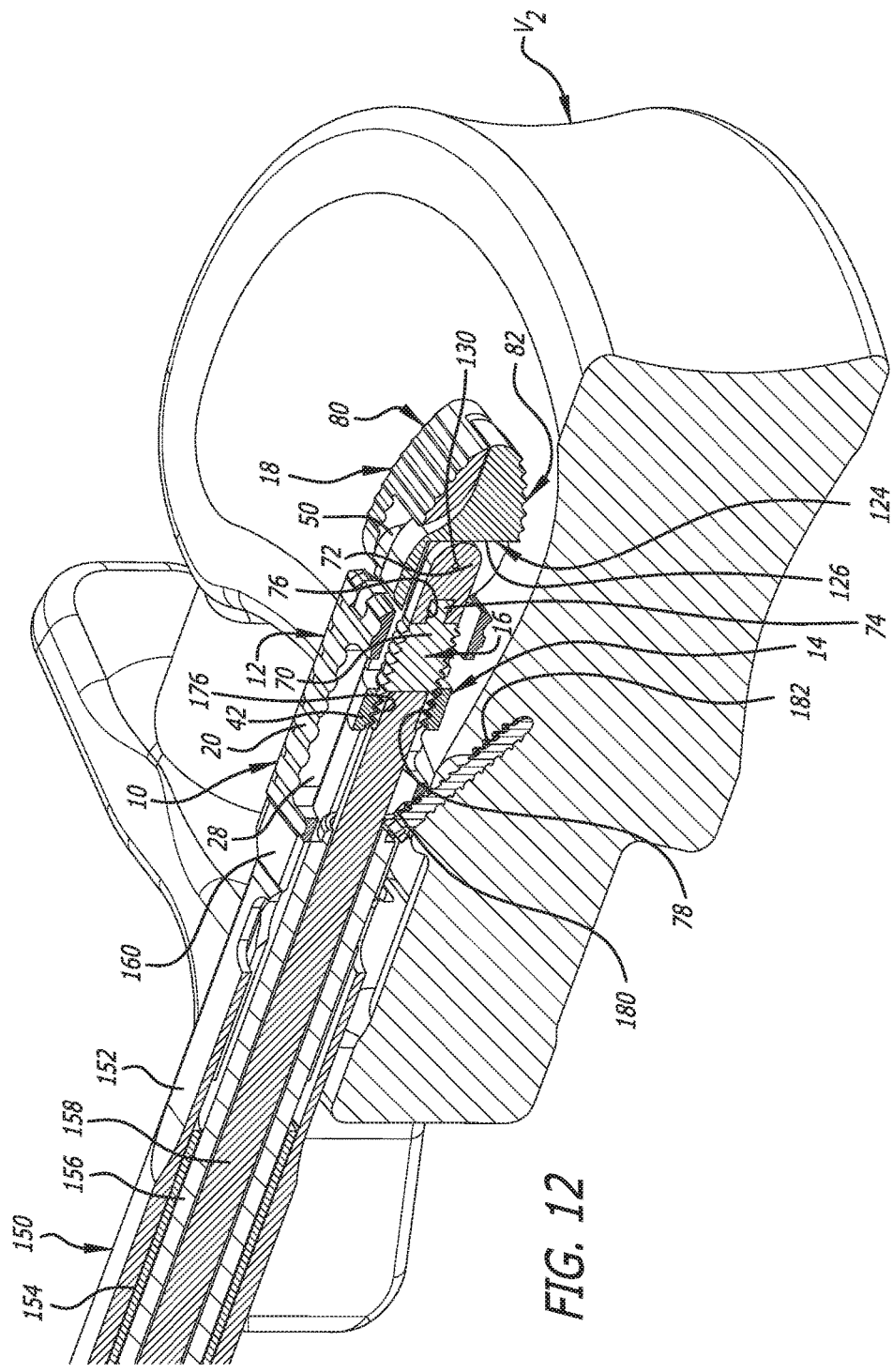
FIG. 12 is a cross-sectional perspective view of the expandable implant of FIG. 1A inserted into the disc space by the insertion instrument prior to moving the carriage portion to the extended position and moving the expandable portion to the open position.
Figure 13:
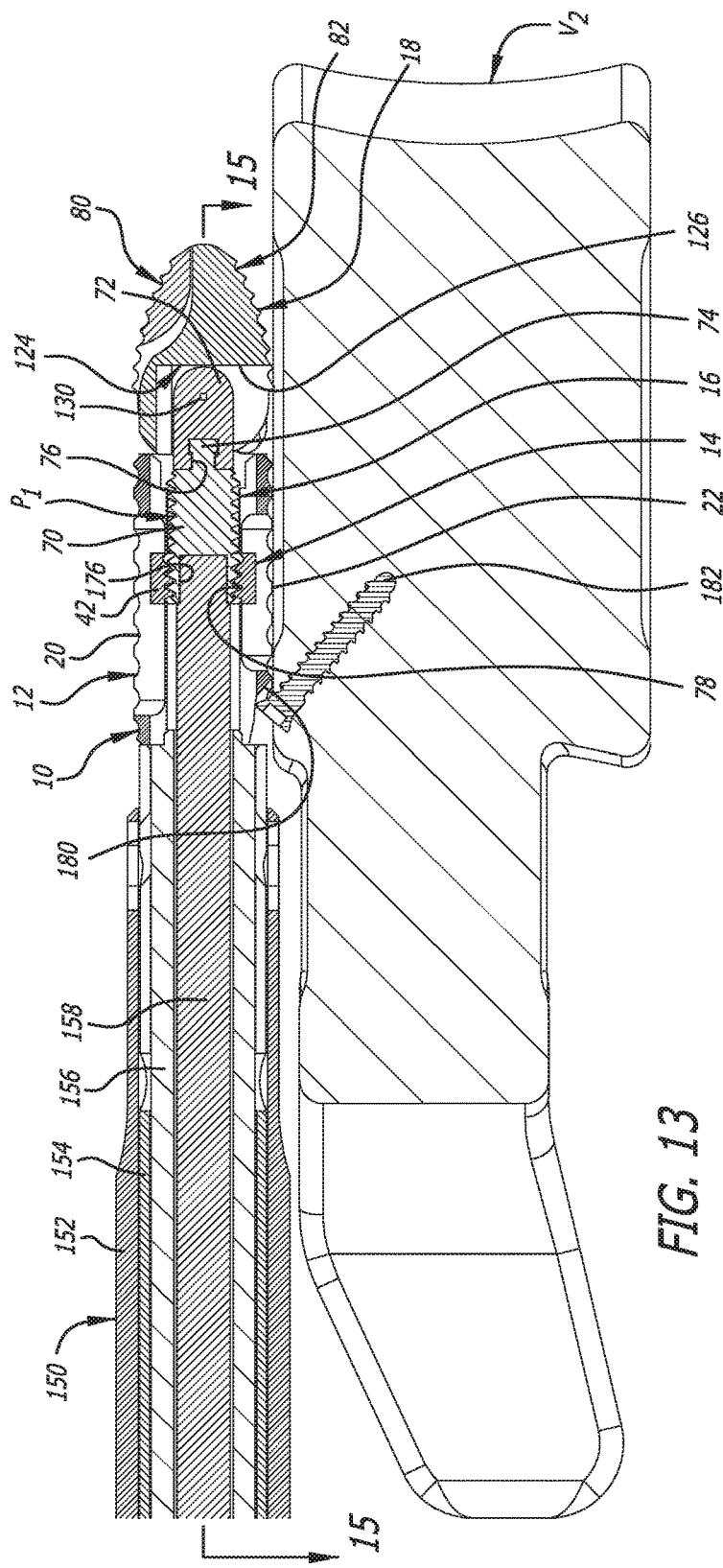
FIG. 13 is a cross-sectional side elevational view of the expandable implant of FIG. 1A inserted into the disc space by the insertion instrument prior to moving the carriage portion to the extended position and moving the expandable portion to the open position.
Figure 14:
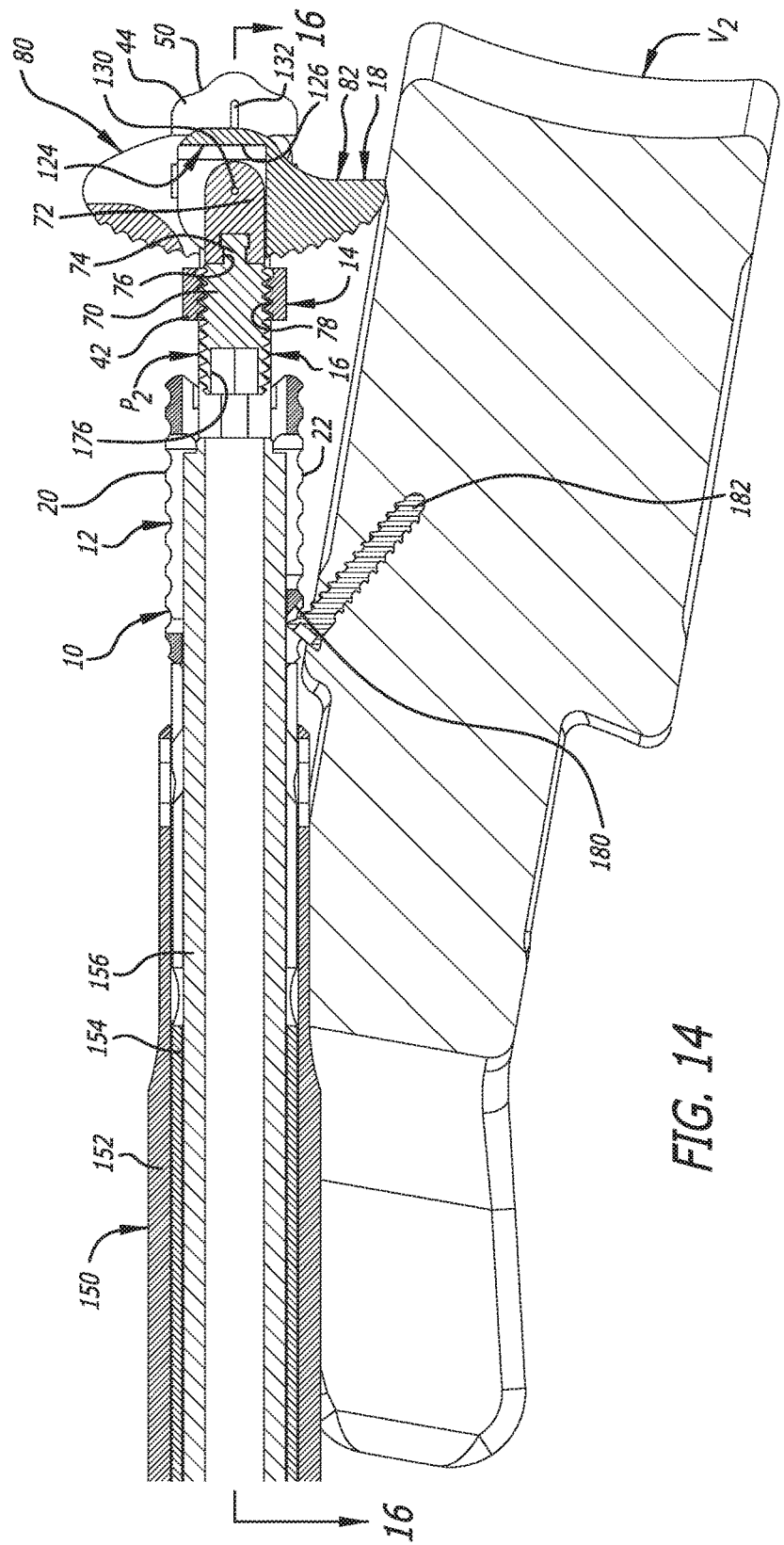
FIG. 14 is a cross-sectional side elevational view of the expandable implant of FIG. 1A inserted into the disc space by the insertion instrument with the carriage portion in the extended position and the expandable portion in the open position.
Figure 15:
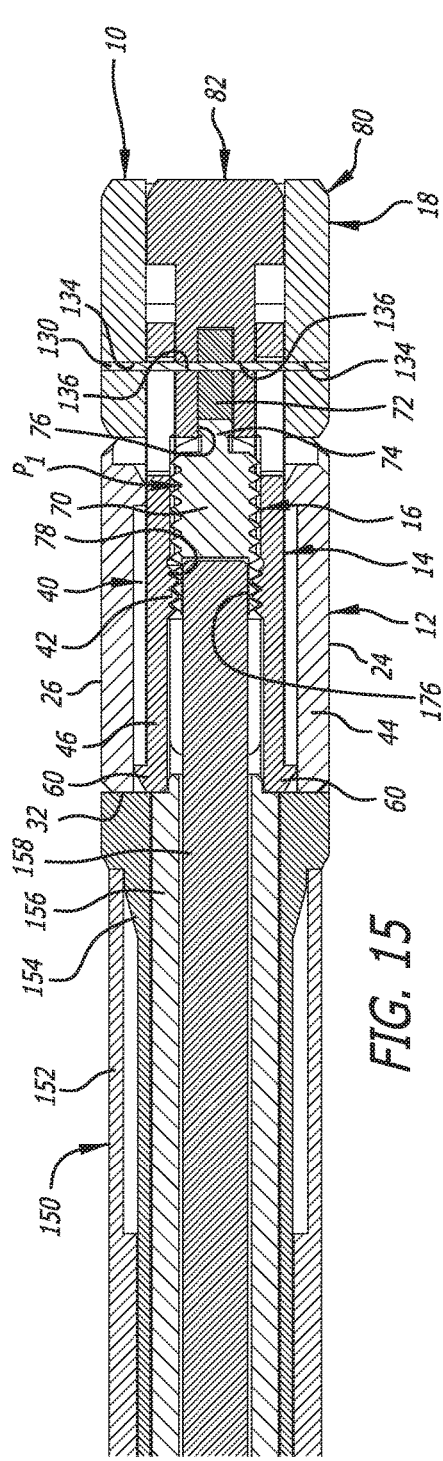
FIG. 15 is a cross-sectional plan view of the expandable implant of FIG. 1A and the insertion instrument along Line 15-15 of FIG. 13.

As depicted in FIG. 12-14, the expandable implant 10 includes a body portion 12, a carriage portion 14, a deployment assembly 16, and an expandable portion 18. As discussed below, the deployment assembly 16 and the expandable portion 18 are attached to the carriage portion 14, and portions of the carriage portion 14 are moveable out of and into the body portion 12. Furthermore, when the expandable implant 10 is inserted into a disc space, the expandable portion 18 is expandable (FIGS. 8-11) to push the upper vertebral body and the lower vertebral body away from one anther.

Figure 4:
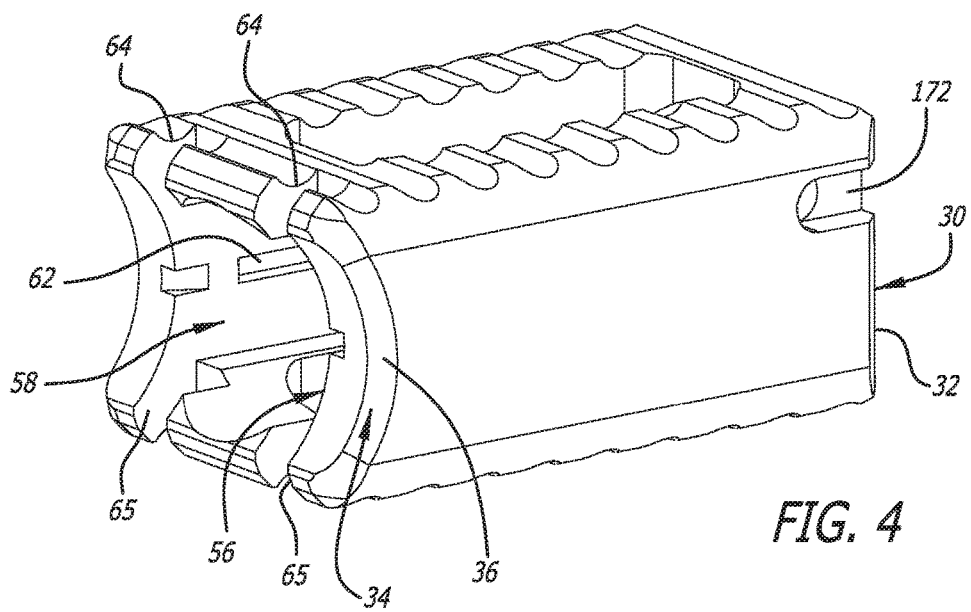
FIG. 4 is a side perspective view of a body portion of the expandable implant of FIG. 1A.
Figure 5:
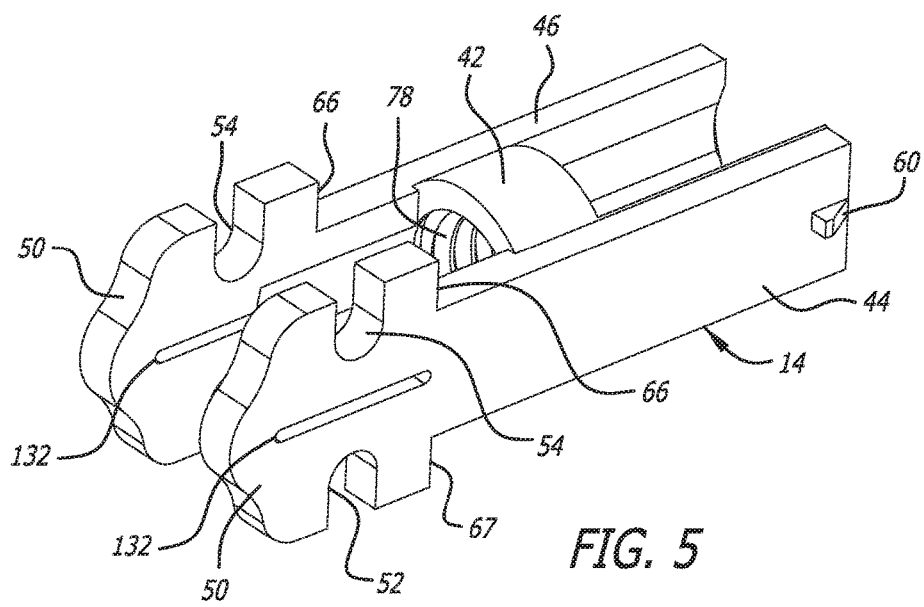
FIG. 5 is a side perspective view of the carriage portion of the expandable implant of FIG. 1A.

As depicted in FIGS. 1A, 1B, and 4, the body portion 12 includes an upper surface 20, a lower surface 22, a first side surface 24, and a second side surface 26. The upper surface 20 and the lower surface 22 can include surface roughenings such as, for example, ribs, ratchets, coatings, growths or positive features, or indents, whether troughs or singly formed pockets. When contacted to the two adjacent vertebral bodies of the vertebrae $V_1$ and $V_2$, the surface roughenings serve in maintaining the position of the body portion 12 in the disc space.

When the expandable implant 10 is configured as a spinal fusion implant, the body portion 12 can include an aperture 28 (FIGS. 1A, 1B, and 4) extending between the upper surface 20 and the lower surface 22. The aperture 28 permits bone growth between the two adjacent vertebral bodies of the vertebrae $V_1$ and $V_2$ through the expandable implant 10.

Furthermore, as depicted in FIGS. 1A, 1B, 3, and 4, the body portion 12 includes a trailing end 30 with a trailing surface 32, and the body portion 12 includes a leading end 34 with a leading surface 36. The body portion 12 also includes a hollow interior 40 extending between the trailing end 30 and the leading end 34. The hollow interior 40 is sized to receive portions of the carriage portion 14 therein, and, as discussed below, portions of the carriage portion 14 are moveable out of and into the hollow interior 40.

Figure 2A:
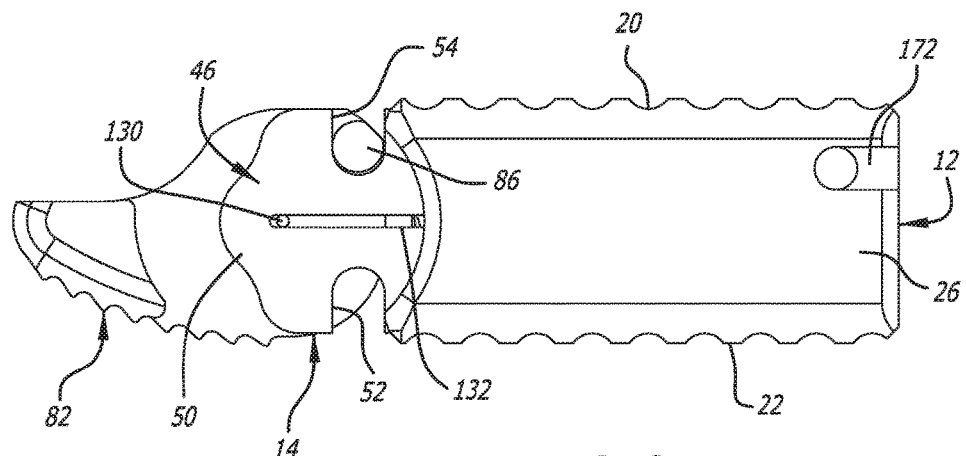
FIG. 2A is a side elevational view of the expandable implant of FIG. 1A with an upper jaw portion removed to show a lower jaw portion in a position corresponding to the closed position of the expandable portion.
Figure 2B:
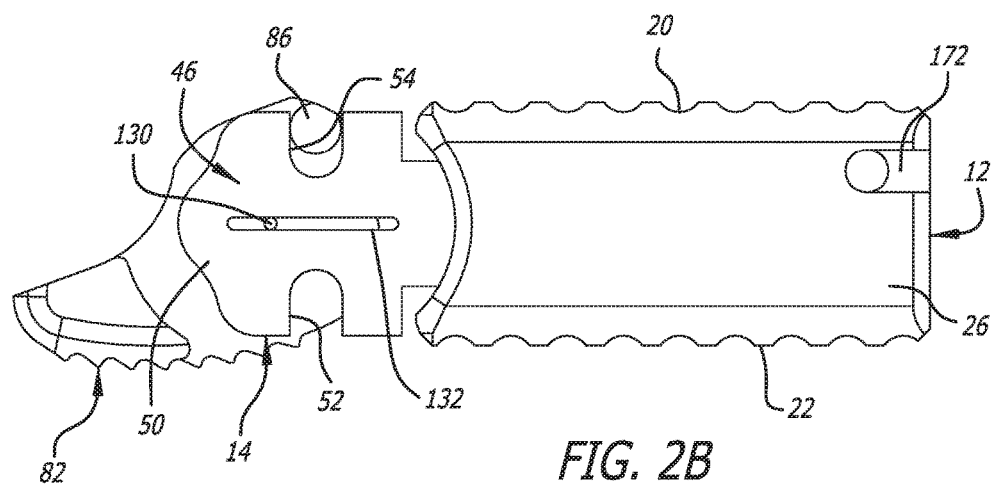
FIG. 2B is a side elevational view of the expandable implant of FIG. 1A with the upper jaw portion removed to show the lower jaw portion in a first intermediate position.
Figure 3:
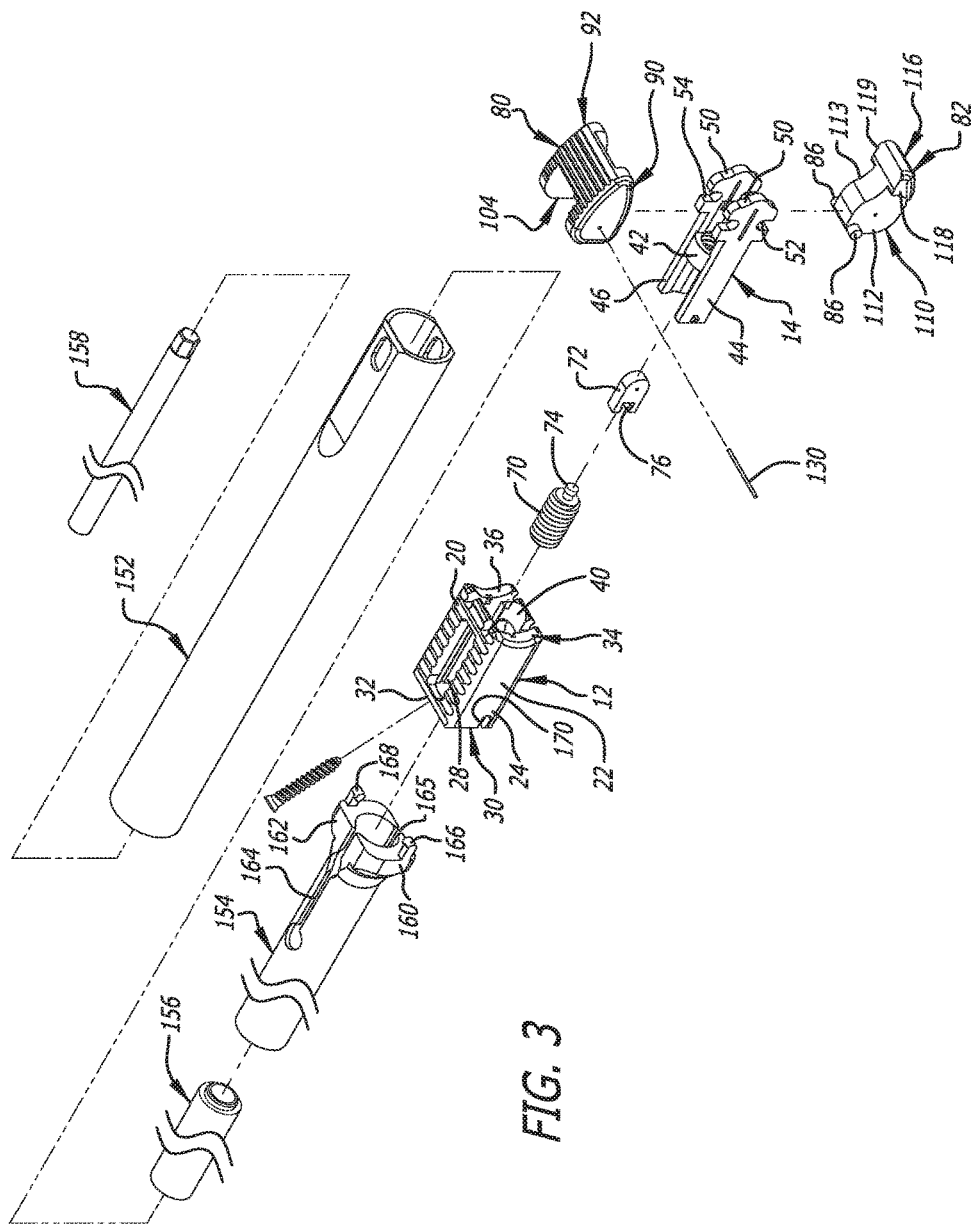
FIG. 3 is an exploded view of the expandable implant of FIG. 1A and an insertion instrument used to insert the expandable implant into a disc space between adjacent vertebral bodies.

As depicted in FIGS. 1B, 3, and 4, the carriage portion 14 includes a collar portion 42, a first arm portion 44, and a second arm portion 46. The collar portion 42 is positioned between the first arm portion 44 and the second arm portion 46. In doing so, the collar portion 42 spaces apart and attaches the first arm portion 44 and the second arm portion 46 to one another. As discussed below, the collar portion 42 is configured to receive a portion of the deployment assembly 16. Each of the first arm portion 44 and the second arm portion 46 includes a head portion 50, and each of the head portions 50 include a first indentation 52 and a second indentation 54. As discussed below, the first indentation 52 and the second indentation 54 are used in engaging portions of the expandable portion 18.

As depicted in FIGS. 1B, 3, 15, and 16, the first arm portion 44 and the second arm portion 46 can be received within the hollow interior 40. Furthermore, the first arm portion 44 and the second arm portion 46 are moveable with respect to the hollow interior 40 between a retracted position (FIG. 1A) and an extended position (FIG. 1B). To facilitate such movement the hollow interior 40 includes a first channel 56 and a second channel 58 for receiving the first arm portion 44 and the second arm portion 46, respectively. The receipt thereof therein constrains the first arm portion 44 to slidable movement in the first channel 56 and constrains the second arm portion 46 to slidable movement in the second channel 58. Each of the first arm portion 44 and the second arm portion 46 includes a detent 60 for receipt in a detent channel 62 correspondingly formed along each of the first channel 56 and the second channel 58. The interaction between the detents 60 and the detent channels 62 serves in inhibiting play of the first arm portion 44 and the second arm portion 46 in the first channel 56 and the second channel 58, respectively. The detent channels 62 also stop short of the leading end surface 36 of the body portion 12. Thus, the first arm portion 44 and the second arm portion 46 are prevented from being removed from the hollow interior 40 by the interaction of the detents 60 in the detent channels 62. As such, portions (i.e., the first arm portion 44 and the second arm portion 46) of the carriage portion 14 are moveable out of and into the body portion 12 in directions toward and away, respectively, from the insertion direction of the expandable implant 10.

The body portion 12 is configured to constrain movement of the carriage portion 14 in directions transverse to the insertion direction when the first arm portion 44 and the second arm portion 46 are fully inserted in the hollow interior 40. The body portion 12 includes notches 64 (FIGS. 1A, 1B, and 4) formed in the upper surface 20 and the leading end surface 36, and the notches 65 formed in the lower surface 22 and leading end surface 36. Furthermore, the head portions 50 of the first arm portion 44 and the second arm portion 46 each include an upper shoulder 66 and a lower shoulder 67. When the first arm portion 44 and the second arm portion 46 are fully inserted in the hollow interior 40, the upper shoulders 66 are received in the notches 64, and the lower shoulders 67 are received in the notches 65. The interaction of the upper shoulders 66 in the notches 64, and the interaction of the lower shoulders 67 in the notches 65 serves to inhibit movement of the carriage portion 14 in directions transverse to the insertion direction of the expandable implant 10.

As depicted in FIGS. 12-16, the deployment assembly 16 includes a deployment screw 70 and a yoke 72 attached to one another. Furthermore, as depicted in FIGS. 3 and 12-14, the deployment screw 70 includes a post 74, and the yoke 72 includes a notch 76 for receiving the post 74. The deployment screw 70, as depicted in FIGS. 3 and 12-14, is received within a threaded hole 78 formed in the collar portion 42. Rotation of the deployment screw 70 within the threaded hole 78 serves to axially move the deployed screw 70 and the yoke 72 attached thereto toward and away from the insertion direction of the expandable implant 10.

The head portion 50 supports the expandable portion 18. The expandable portion 18 includes an upper jaw portion 80 and a lower jaw portion 82. The upper jaw portion 80 include pegs 84 (FIGS. 1A and 6), and the lower jaw portion 82 includes pegs 86 (FIGS. 2A-2D and 7). As discussed above, the first indentations 52 and the second indentations 54 of the head portion 50 are used in engaging portions of the expandable portion 18. To that end, the pegs 84 of the upper jaw portion 80 are received in the first indentations 52, and the pegs 86 of the lower jaw portion 82 are received in the second indentations 54. As discussed below, the interaction of the pegs 84 in the first indentions 52, and the interaction of the pegs 86 in the second indentations 54 provides support therefor and allows pivotal movement of the upper jaw portion 80 and the lower jaw portion 82 of the expandable portion 18.

Figure 6:
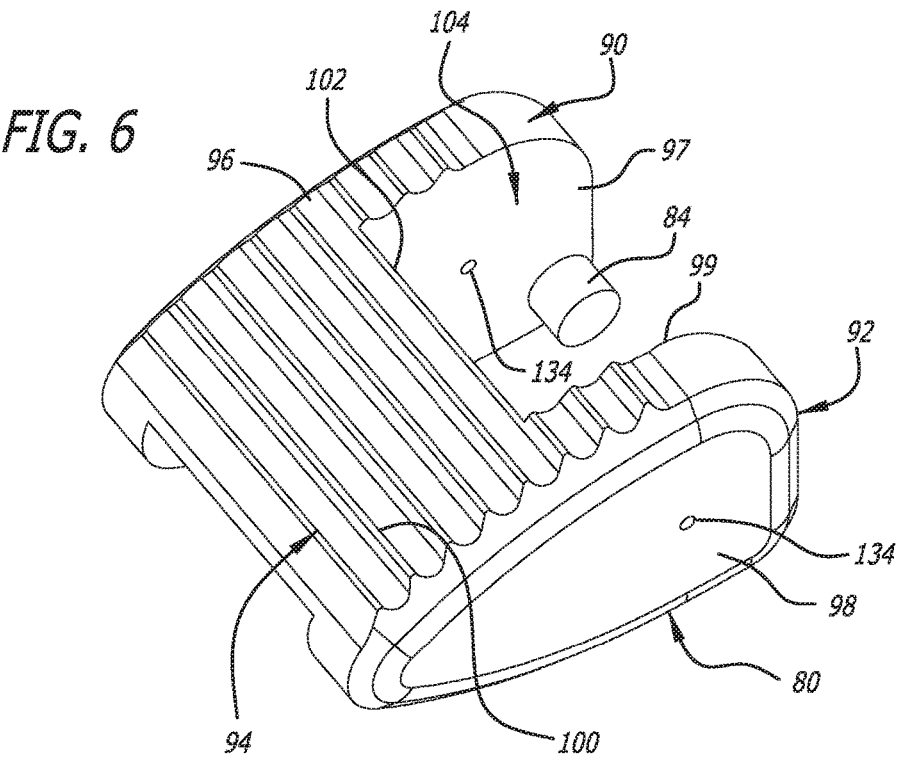
FIG. 6 is a bottom perspective view of the upper jaw portion of the expandable portion.

The upper jaw portion 80, as depicted in FIG. 6, includes a first sidewall 90, a second sidewall 92, and an upper wall 94 connecting the first sidewall 90 and the second sidewall 92 to one another. The first sidewall 90 includes an outer surface 96 and an inner surface 97, and the second sidewall 92 includes an outer surface 98 and an inner surface 99. Furthermore, the upper wall 94 includes an outer surface 100 for engaging the upper of the two adjacent vertebral bodies of the vertebrae $V_1$ and $V_2$, and inner surface 102. Together, the inner surface 97, the inner surface 99, and the inner surface 102 form a cavity 104 for receiving portions of the head portions 50, and the pegs 84 extend from the inner surface 97 and the inner surface 99.

Figure 7:
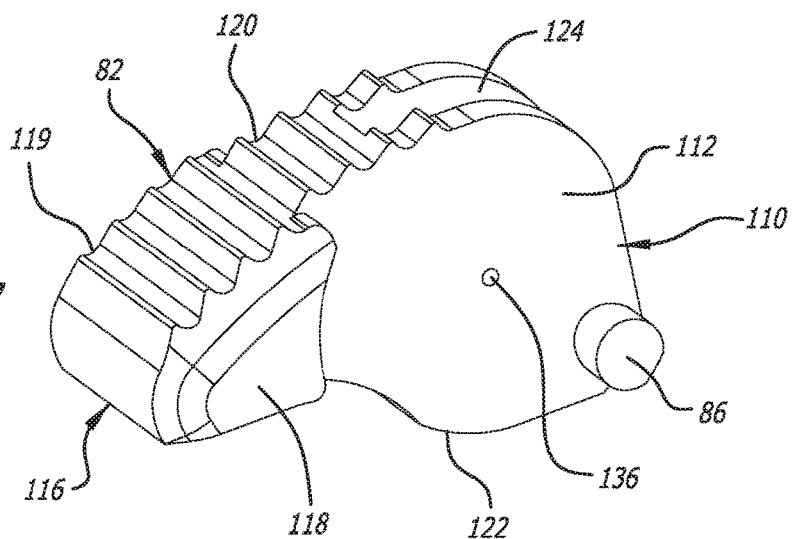
FIG. 7 is a top perspective view of the lower jaw portion of the expandable portion.

The lower jaw portion 82, as depicted in FIG. 7, includes a first body portion 110 having a first outer surface 112 and a second outer surface 113, and a second body portion 116 having a first outer surface 118 and a second outer surface 119. The first body portion 110 and the second body portion 116 share an outer surface 120 and an inner surface 122. An indentation 124 with a shoulder 126 is formed in the first body portion 110 for receiving the yoke 72 therein. The first body portion 110 is received between portions of the head portions 50, and the pegs 86 extend from the first outer surface 112 and the second outer surface 113.

As depicted in FIGS. 1A, 1B, and 3, the expandable portion 18 is attached to the head portions 50 of the first arm portion 44 and the second arm portion 46. When the upper jaw portion 80 is attached to the head portions 50, portions of the head portions 50 are received in the cavity 104, and the pegs 84 are received in the first indentations 52. Furthermore, when the lower jaw portion 82 is attached to the head portions 50, portions of the first body portion 110 are received between the head portions 50, and the pegs 86 are received in the second indentations 54. The upper jaw portion 80 and the lower jaw portion 82 are securely attached to the head portions 50 using a pin 130. Each of the head portions 50 include a pin-receiving slot 132, the sidewalls 90 and 92 of the upper jaw portion 80 each include a pin-receiving hole 134, and the first body portion 110 includes a pin-receiving hole 136. The pin 130 is positioned through the pin-receiving slots 132, the pin-receiving holes 134, and the pin-receiving hole 136 to securely attach the upper jaw portion 80 and the lower jaw portion 82 to the carriage portion 14.

The interaction of the pegs 84 in the first indentations 52, the interaction of the pegs 86 in the second indentations 54 (FIGS. 2A-2D), and the interactions of the pin 130 in the pin-receiving slots 132 allow for corresponding pivotal movement and slidable movement of the upper jaw portion 80 and the lower jaw portion 82 with respect to the carriage portion 14. Such pivotal and slidable movement allows the upper jaw portion 80 and the lower jaw portion 82 to open and close with respect to one another, as depicted in FIGS. 1A, 1B, 2A-2D, 9-11, 13, and 14.

Figure 16:
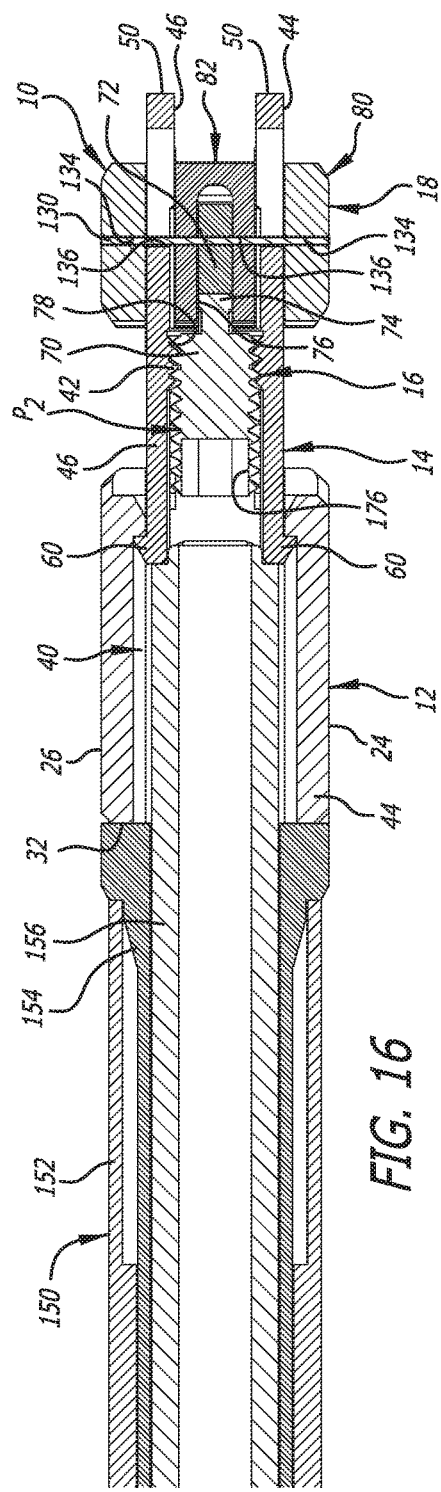
FIG. 16 is a cross-sectional plan view of the expandable implant of FIG. 1A and the insertion instrument along Line 16-16 of FIG. 14.

The deployment screw 70 is moveable at least from between a first position $P_1$ (FIGS. 13 and 15) and a second position $P_2$ (FIGS. 14 and 16). In the first position $P_1$, the deployment screw 70 has been rotated toward the distal end $E_1$ of the expandable implant 10 in the direction of insertion thereof, and, in the second position $P_2$, the deployment screw 70 has been rotated toward the proximate end $E_2$ of the expandable implant 10 away from the insertion direction thereof.

When moved toward the first position $P_1$, the deployment screw 70 pushes the yoke 72 and the pin 130 attached thereto to thereby move the upper jaw portion 80 and the lower jaw portion 82 toward the distal end $E_1$ until the pin 130 contacts the distal ends of the pin-receiving slots 132. When the pin 130 is moved toward and contacted with the distal ends of the pin-receiving slots 132, the geometry and interaction of the pegs 84 in the first indentations 52 and of the pegs 86 in the second indentations 54 force the upper jaw portion 80 and the lower jaw portion 82 closed.

When moved toward the second position $P_2$, the deployment screw 70 retracts the yoke 72 and the pin 130 attached thereto to thereby move the upper jaw portion 80 and the lower jaw portion 82 toward the proximate end $E_2$ until the pins 130 contacts the proximal ends of the pin-receiving slots 132. When the pin 130 is moved toward and contacted with the proximal ends of the pin-receiving slots 132, the corresponding geometry and interaction of the pegs 84 in the first indentations 52 and of the pegs 86 in the second indentations 54 force the upper jaw portion 80 and the lower jaw portion 82 open.

The outer surface 100 of the upper jaw portion 80 and the outer surface 120 of the upper jaw portion 82 can include surface roughenings such as, for example, ribs or ratchets. When contacted to the two adjacent vertebral bodies of the vertebrae $V_1$ and $V_2$, the surface roughenings serve in resisting movement of the expandable portion 18.

The expandable implant 10 is inserted into the disc space using an insertion instrument 150. The insertion instrument 150 is also configured to push the carriage portion 14 in the direction of insertion, and to rotate the deployment screw 70. As discussed above, portions of the carriage portion 14 are moveable out of and into the body portion 12. The insertion instrument 150 is configured to facilitate at least movement of portions of the carriage portion 14 out of the body portion 12. Furthermore, as discussed above, when the deployment screw 70 is in the first position $P_1$, the upper jaw portion 80 and the lower jaw portion 82 are closed, and, when the deployment screw 70 is in the second position $P_2$, the upper jaw portion 80 and the lower jaw portion 82 are opened. The insertion instrument 150 is configured to facilitate rotation of the deployment screw 70 and its corresponding movement between the first position $P_1$ and the second position $P_2$.

As depicted in FIGS. 3 and 12-14, the insertion instrument 150 includes a first sleeve 152, a second sleeve 154, a pusher tool 156, and a driver tool 158. The driver tool 158 is received in the pusher tool 156, and the pusher tool 156 is received in the second sleeve 154. Furthermore, the second sleeve 154 is received in the first sleeve 152, and the second sleeve 154 includes a first arm section 160 and a second arm section 162. The first arm section 160 and the second arm section 162 are separated by an upper slot 164 and a lower slot 165. The first arm section 160 and the second arm section 162 are biased away from one another, and the first arm section 160 includes a first detent 166 and the second arm section 162 includes a second detent 168. The first detent 166 is configured for receipt in a first detent-receiving hole 170 formed in the body portion 12, and the second detent 168 is configured for receipt in a second detent-receiving hole 172 formed in the body portion 12.

When received therein, movement of the second sleeve 154 into the first sleeve 152 forces the first arm section 160 and the second arm section 162 towards one another. In doing so, the first detent 166 and the second detent 168 are also moved towards one another. Thus, when the expandable implant 10 is properly positioned with respect to the insertion instrument 150, the interaction of the first sleeve 152 and the second sleeve 154 can force the first detent 166 and the second detent 168 into the first detent-receiving hole 170 and the second detent-receiving hole 172, respectively. The interaction between the first detent 166 and the second detent 168 in the first detent-receiving hole 170 and the second detent-receiving hole 172, respectively, attaches the expandable implant 10 to the insertion instrument 150.

With the expandable implant 10 attached to the insertion instrument 150, the driver tool 158 can be engaged with the deployment screw 70 (via a tool-receiving aperture 176) to move it into position $P_1$. With the deployment screw 70 in position $P_1$, the upper jaw portion 80 and the lower jaw portion 82 are in the closed position. When the upper jaw portion 80 and the lower jaw portion 82 are in the closed position, the expandable implant 10 can be inserted into the disc space between the two vertebral bodies.

During insertion of the expandable implant 10 into the disc space, the interaction of the outer surface 100 of the upper jaw portion 80 and the outer surface 120 of the lower jaw portion 82 with the two adjacent vertebral bodies of the vertebrae $V_1$ and $V_2$ forces portions of the carriage portion 14 to remain inside the hollow interior 40 of the body portion 12.

Once positioned in the disc space, the driver tool 158 can be used to rotate the deployment screw 70, and correspondingly move the deployment screw 70 from position $P_1$ (FIGS. 13 and 15) toward position $P_2$ (FIGS. 14 and 16). Movement of the deployment screw 70 from position $P_1$ to position $P_2$ serves in opening the upper jaw portion 80 and the lower jaw portion 82. With the deployment screw 70 in position $P_2$, the upper jaw portion 80 and the lower jaw portion 82 are in the open position. Furthermore, the pusher tool 156 facilitates at least movement of portions of the carriage portion 14 out of the body portion 12. That is, the pusher tool 156 can be used to move the carriage portion 14 (and the expandable portion 18 supported by the carriage portion 14) from a retracted position (FIG. 1A) to an expanded position (FIG. 1B). Resistance due to the interaction of the upper jaw portion 80 and the lower jaw portion 82 with the two adjacent vertebral bodies of the vertebrae $V_1$ and $V_2$ tends to force the upper jaw portion 80 and the lower jaw portion 82 to move backwards relative to the first arm portion 44 and the second arm portion 46 such that the pin 130 is forced proximally in the pin-receiving slots 132. Furthermore, when portions of the carriage portion 14 are moved out of the body portion 12 by the pusher tool 156 in the direction of insertion, the pin 130 also is correspondingly forced towards the proximal ends of the pin-receiving slots 132 by resistance due to the interaction of the upper jaw portion 80 and the lower jaw portion 82 with the two adjacent vertebral bodies of the vertebrae $V_1$ and $V_2$.

When the upper jaw portion 80 and the lower jaw portion 82 are opened in the disc space, the two adjacent vertebral bodies of the vertebrae $V_1$ and $V_2$ are correspondingly moved apart from one another (FIGS. 8-11). As such, after being positioned in the disc space, the expandable implant 10, via actuation by the insertion instrument 150, can be used to distract the adjacent vertebrae $V_1$ and $V_2$ apart from one another.

With the current embodiment, both the upper jaw portion 80 and the lower jaw portion 82 are shown to pivot and open. Alternatively, the carriage portion 14 and one of the upper jaw portion 80 and the lower jaw portion 82 may be made integral such that, when the device is opened, only the other of the upper jaw portion 80 and the lower jaw portion 82 is pivoted. Also, the range of movement of the pin 130 in the pin-receiving slot 132 can be decreased or increased to correspondingly alter the range of movement of the upper jaw portion 80 and the lower jaw portion 82. To illustrate, the length of the slot 132 can be shortened to correspondingly decrease the amount by which the upper jaw portion 80 and the lower jaw portion 82 can be opened, or the length of the slot 132 can be lengthened to correspondingly increase the amount by which the upper jaw portion 80 and the lower jaw portion 82 can be opened. Thus, if different force requirements were needed on the pegs 84 and 86, or different degrees of deployment of the upper jaw portion 80 and lower jaw portion 82 were needed, the range of angulation of the upper jaw portion 80 and the lower jaw portion 82 could be changed by correspondingly altering the length of the pin-receiving slot 132.

With the current embodiment, the yoke 72 is shown to pull the upper jaw portion 80 and the lower jaw portion 82 into the open position. Alternatively, the expandable implant 10 could be configured such that the yoke 72 could be pushed to move the upper jaw portion 80 and the lower jaw portion 82 into the open position.

As the upper jaw portion 80 and the lower jaw portion 82 are expanded, the two adjacent vertebral bodies of the first upper vertebrae $V_1$ and the second lower vertebrae $V_2$ would be supported on the tips of the upper jaw portion 80 and the lower jaw portion 82 and a proximal portion of the body portion 12 (FIGS. 9-11). It is contemplated that pivotable struts (not shown) could be included with the upper jaw portion 80 and the lower jaw portion 82 that extend toward the body portion 12 and span from adjacent the distal end $E_2$ to adjacent the proximal end $E_1$, such that, as the upper jaw portion 80 and the lower jaw portion 82, are expanded the struts would travel with the upper jaw portion 80 and the lower jaw portion 82 to bridge the gap between adjacent the tips of the upper jaw portion 80 and the lower jaw portion 82 and adjacent a proximal portion of the body portion 12. Alternatively, the struts could also be pivotally engaged with the body portion 12 and allowed to ride in grooves in the upper jaw portion 80 and the lower jaw portion 82 to provide such a bridge As can be appreciated from FIGS. 8-11, as the expandable implant 10 is expanded, the adjacent vertebral bodies of the first upper vertebrae $V_1$ and the second lower vertebrae $V_2$ are angled, or put in lordosis, since the vertebral bodies are contacted with the tips of the upper jaw portion 80 and the lower jaw portion 82 and a proximal portion of the body portion 12. The expandable implant 10 could also be reversed so that the expansion would cause the adjacent vertebral bodies to go into kyphosis. Also, its contemplated that, as the first arm portion 44 and the second arm portion 46 move through the body portion 12, ramps on the first channel 56 and the second channel 58 could cause the body portion 12 to expand, giving modest amounts of posterior height increase thereto.

As depicted in FIGS. 1A and 1B, portions of the lower jaw portion 82 are positioned between inner surfaces 97 and 99 of the upper jaw portion 80 of the first sidewall 90 and the second sidewall 92, respectively. Alternatively, it is contemplated that the first sidewall 90 of the upper jaw portion 80 could remain on the outside, but that the second sidewall 92 of the upper jaw portion could reside between the first arm portion 44 and the second arm portion 46 of the carriage portion 14. Similarly, the lower jaw portion 82 could be configured to have one outer sidewall on the outside and one inner sidewall residing between the first arm portion 44 and the second arm portion 46 of the carriage portion 14. Such are configuration would afford alternating position of the sidewalls.

Movement of portions of the carriage portion 14 out of the body portion 12 depends at least in part on the stationary position of the body portion 12 between the two adjacent vertebral bodies of the vertebrae $V_1$ and $V_2$. As discussed above, the upper surface 20 and the lower surface 22 of the body portion 12 can include surface roughenings that serve in maintaining the position of the body portion 12 in the disc space. However, if additional security is required, the body portion 12, as depicted in FIGS. 2 and 12-14 can include an aperture 180 for receiving a bone screw 182. The bone screw 182 can be inserted through the aperture 180 and into one of the two adjacent vertebral bodies of the vertebrae $V_1$ and $V_2$ to securely attach the body portion 12 thereto.

Figure 17:
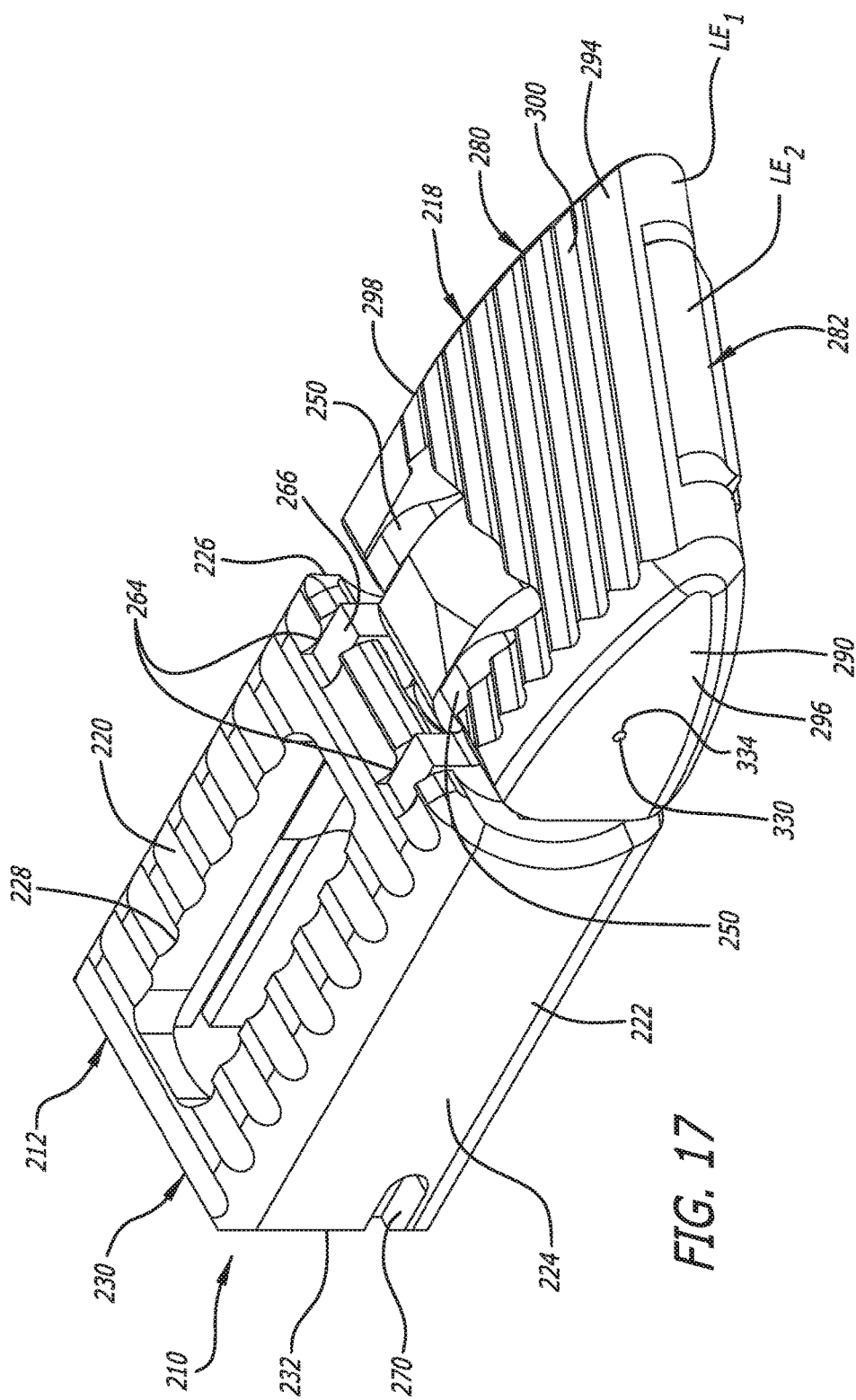
FIG. 17 is a perspective view of a second embodiment of an expandable implant according to the present invention depicting a carriage portion thereof positioned in a retracted position and an expandable portion thereof in a closed position.
Figure 18:
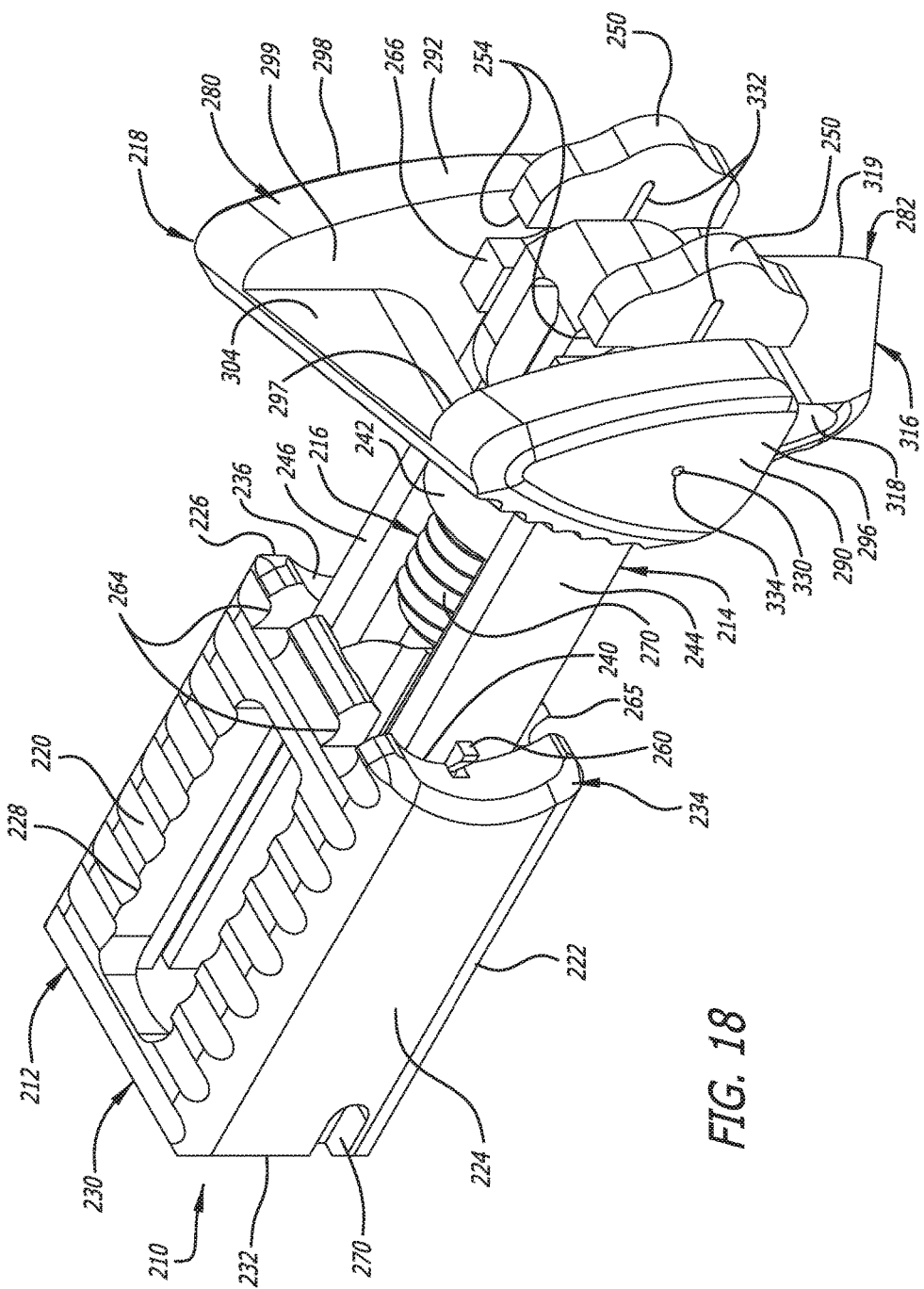
FIG. 18 is a perspective view of the expandable implant of FIG. 17 depicting the carriage portion in an extended position and the expandable portion thereof in an open position.
Figure 19:
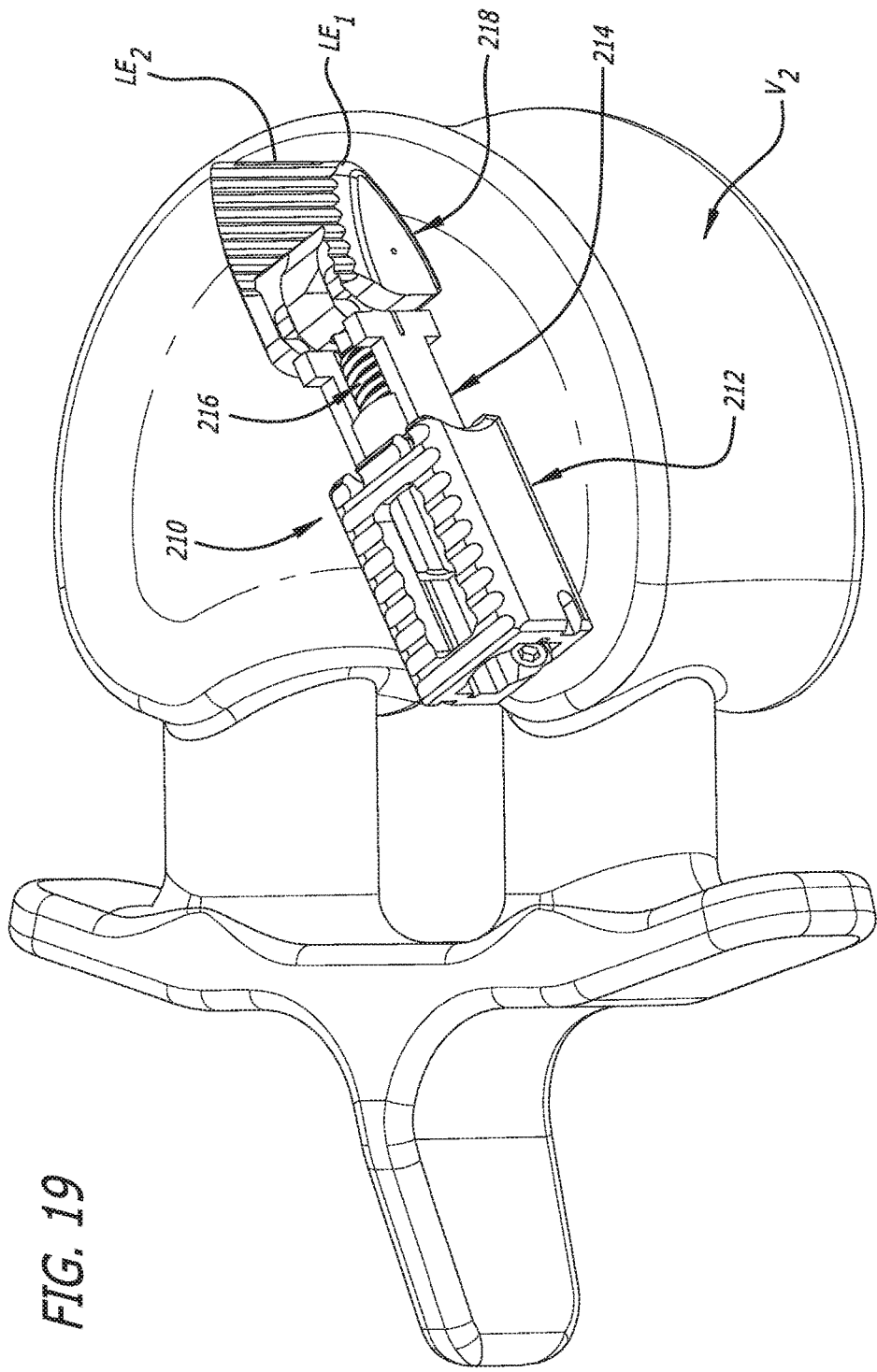
FIG. 19 is a perspective view of the expandable implant of FIG. 17 inserted into a disc space by the insertion instrument after the moving the carriage portion to the extended position, but prior to moving the expandable portion to the open position.

Another embodiment of the expandable implant of the present invention is generally indicated by the numeral 210 in FIGS. 17-19. The expandable implant 210 includes many of the same features of the expandable implant 10, and thus, like numerals are used in labeling the features of the expandable implant 210. Furthermore, like the expandable implant 10, the expandable implant 210 can be inserted into the disc space D using the insertion instrument 150. However, unlike that of the expandable implant 10, the expandable portion 218 of the expandable implant 210 includes an angled leading end. The leading ends of the upper jaw portion 80 and the lower jaw portion 82 of the expandable implant 10 are perpendicular to the direction of insertion of the expandable implant 10. In contrast, as depicted in FIGS. 17 and 19, the leading end $LE_1$ of the upper jaw portion 280 and the leading end $LE_2$ of the lower jaw portion 282 are angled with respect to the direction of insertion and would allow for the leading end $LE_1$ and the leading end $LE_2$ of the expandable implant 210 to better engage the anterior lips of the adjacent vertebral bodies.

As shown in the images of device 210, the vertebral body engaging features run parallel to the tip angulation to provide engagement of the bone in the direction of the tip angle.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

I claim:

1. An expandable spinal implant for insertion in a disc space between adjacent upper and lower vertebral bodies and an insertion instrument releasably attachable to the expandable implant, the expandable spinal implant comprising:
a body portion having a first end, an opposite second end, and an interior cavity;
a carriage portion having a first arm portion, a second arm portion, and a collar portion attaching the first arm portion and the second arm portion to one another, the first arm portion and the second arm portion each including a slot extending therealong, the slot being configured to receive a pin, portions of the first arm portion and the second arm portion being receivable within the interior cavity of the body portion, and the first arm portion and the second arm portion being moveable between a retracted position and an expanded position relative to the interior cavity of the body portion, the collar portion including a threaded aperture extending therethrough;
an expandable portion supported by the first arm portion and second arm portion, the expandable portion including an upper portion and a lower portion, the upper portion and the lower portion being attached to the first arm portion and the second arm portion, the upper portion having at least one aperture therein and the lower portion having an aperture therein, the apertures receiving the pin therethrough to attach the upper portion and the lower portion to the first arm portion and the second arm portion; and
a deployment portion including a deployment screw and a yoke portion engaging the deployment screw, at least a portion of the deployment screw being received in the threaded aperture of the collar portion, and the yoke portion including an aperture therein for receiving the pin therethrough to attach the yoke portion to the upper portion, the lower portion, and the first arm portion and the second arm portion, the deployment screw being moveable between a first position and a second position via rotation thereof with respect to the threaded aperture of the collar portion;
the insertion instrument comprising:
at least one sleeve portion having at least one aperture extending therethrough; and
a pusher portion and a driver portion, the driver portion being partially received and slidable within the pusher portion, and the pusher portion being partially received and slidable within the at least one aperture of the at least one sleeve portion, the pusher portion, when the expandable spinal implant is releasably attached to the insertion instrument, being capable of pushing the carriage portion from the retracted position to the expanded position, and the driver portion, when the expandable spinal implant is releasably attached to the insertion instrument, being capable of rotating the deployment screw,
wherein rotational movement of the deployment screw via rotation of the driver portion serves to move the yoke portion and the pin received therethrough along the slots of the carriage portion, and movement of the pin in the slots serves to move the upper and lower portions between a closed position and an open position.

2. The expandable spinal implant and the insertion instrument of claim 1, wherein the upper portion includes at least one peg for engaging one of the first arm portion and the second arm portion, and the lower portion includes at least one peg for engaging one of the first arm portion and the second arm portion, the at least one peg of the upper portion being received in a first indentation in at least one of the first arm portion and the second arm portion, and the at least one peg of the lower portion being received in a second indentation in at least one of the first arm portion and the second arm portion.

3. The expandable spinal implant and the insertion instrument of claim 2, wherein the interaction of the at least one peg of the upper portion in the first indentation creates a first pivot point for pivoting the upper portion due to the movement of the pin in the slots of the first arm portion and the second arm portion, and the interaction of the at least one peg of the lower portion in the second indentation creates a second pivot point for pivoting the lower portion due to the movement of the pin in the slots of the first arm portion and the second arm portion.

4. The expandable spinal implant and the insertion instrument of claim 3, wherein pivotal movement of the upper portion about the first pivot point and pivotal movement of the lower portion about the second pivot point serves to open and close the expandable portion.

5. The expandable spinal implant and the insertion instrument of claim 1, wherein the at least one sleeve includes a first sleeve portion and a second sleeve portion, the second sleeve portion being partially received in the first sleeve portion, the first sleeve portion including a first end and a second end opposite from one another, the second sleeve portion including a first end and a second end opposite from one another, the second sleeve portion including a first arm section and a second arm section adjacent the first end thereof, the first arm section and the second arm section being biased away from one another, wherein, when the second sleeve portion is received in the first sleeve portion, movement of the first end of the first sleeve toward the first end of the second sleeve portion serves to push the first arm portion and the second arm portion toward one another.

6. The expandable spinal implant and the insertion instrument of claim 5, the expandable spinal implant further comprising a first detent-receiving hole and a second detent-receiving hole therein, and the insertion instrument further comprising a first detent provided on the first arm section and a second detent provided on the second arm section, wherein, when the first arm section and the second arm section are moved towards one another, the first detent is receivable in the first detent-receiving hole, and the second detent is receivable in the second detent-receiving hole, the expandable spinal implant being releasably attached to the second sleeve portion with the first detent inserted into the first detent-receiving hole and the second detent inserted into the second detent-receiving hole.

7. The expandable spinal implant and the insertion instrument of claim 1, wherein the body portion includes an upper surface and a lower surface, the upper surface and the lower surface each including surface roughenings for engaging surfaces of the endplates of the upper and lower vertebral bodies to inhibit movement of the body portion when positioned therebetween during movement of the carriage portion from the retracted position to the extended position, and during movement of the upper portion and the lower portion between the closed position and the open position.

8. The expandable spinal implant and the insertion instrument of claim 7, the expandable implant further comprising apertures through the upper surface and the lower surface of the body portion, the apertures communicating with the interior cavity and permitting bone growth between the upper and lower vertebral bodies to facilitate fusion thereof.

9. The expandable spinal implant and the insertion instrument of claim 1, wherein the upper portion and the lower portion of the expandable portion each include an exterior surface including surface roughenings for engaging the surfaces of the endplates of the upper and lower vertebral bodies.

10. An expandable spinal implant for insertion in a disc space between adjacent upper and lower vertebral bodies and an insertion instrument releasably attachable to the expandable implant,
the expandable spinal implant comprising:
a body portion having a end, an opposite second end, and an interior cavity;
a carriage portion including a threaded aperture therethrough, portions of the carriage portion being receivable within the interior cavity of the body portion, the carriage portion being moveable between a retracted position and an expanded position relative to the interior cavity of the body portion, and the carriage portion including at least one slot therethrough, the at least one slot being configured to receive a pin;
an expandable portion supported by the carriage portion, the expandable portion including a first portion and a second portion, the first portion having at least one aperture therein and the second portion having an aperture therein, the apertures receiving the pin therethrough to attach the first portion and the second portion to the carriage portion; and
a deployment portion including a deployment screw and a yoke portion engaging the deployment screw, at least a portion of the deployment screw being received in the threaded aperture of the carriage portion, and the yoke portion including an aperture therein for receiving the pin therethrough to attach the yoke portion to the first portion, the second portion, and the carriage portion, the deployment screw being moveable between a first position and a second position via rotation thereof with respect to the threaded aperture of the carriage portion;
the insertion instrument comprising:
at least one sleeve portion having at least one aperture extending therethrough; and
a pusher portion and a driver portion, the driver portion being partially received and slidable within the pusher portion, and the pusher portion being partially received and slidable within the at least one aperture of the at least one sleeve portion, the pusher portion, when the expandable spinal implant is releasably attached to the insertion instrument, being capable of pushing the carriage portion from the retracted position to the expanded position, and the driver portion, when the expandable spinal implant is releasably attached to the insertion instrument, being capable of rotating the deployment screw,
wherein rotational movement of the deployment screw serves to move the yoke portion and the pin received therethrough along the at least one slot of the carriage portion, and movement of the pin in the at least one slot serves to move the first portion and the second portion of the expandable portion between a closed position and an open position.

11. The expandable spinal implant and the insertion instrument of claim 10, wherein the first portion includes at least one peg for engaging the carriage portion, and the second portion includes at least one peg for engaging the carriage portion, the at least one peg of the first portion being received in a first indentation in the carriage portion, and the at least one peg of the second portion being received in a second indentation in the carriage portion.

12. The expandable spinal implant and the insertion instrument of claim 11, wherein the interaction of the at least one peg of the first portion in the first indentation creates a first pivot point for pivoting the second portion due to the movement of the pin in the at least one slot of the carriage portion, and the interaction of the at least one peg of the first portion in the second indentation creates a second pivot point for pivoting the second portion due to the movement of the pin in the at least one slot of the carriage portion.

13. The expandable spinal implant and the insertion instrument of claim 12, wherein pivotal movement of the first portion about the first pivot point and pivotal movement of the second portion about the second pivot point serves to open and close the expandable portion.

14. The expandable spinal implant and the insertion instrument of claim 10, wherein the at least one insertion instrument includes a first sleeve portion and a second sleeve portion, the second sleeve portion being partially received in the first sleeve portion, the first sleeve portion including a first end and a second end opposite from one another, the second sleeve portion including a first end and a second end opposite from one another, the second sleeve portion including a first arm section and a second arm section adjacent the first end thereof, the first arm section and the second arm section being biased away from one another, wherein, when the second sleeve portion is received in the first sleeve portion, movement of the first end of the first sleeve toward the first end of the second sleeve portion serves to push the first arm portion and the second arm portion toward one another.

15. The expandable spinal implant and the insertion instrument of claim 14, the expandable spinal implant further comprising a first detent-receiving hole and a second detent-receiving hole formed therein, and the insertion instrument further comprising a first detent provided on the first arm section and a second detent provided on the second arm section, wherein, when the first arm section and the second arm section are moved towards one another, the first detent is receivable in the first detent-receiving hole, and the second detent is receivable in the second detent-receiving hole, the expandable spinal implant being releasably attached to the second sleeve portion with the first detent inserted into the first detent-receiving hole and the second detent inserted into the second detent-receiving hole.

16. The expandable spinal implant and the insertion instrument of claim 1, wherein the first portion and the second portion of the expandable portion each include an exterior surface including surface roughenings for engaging the surfaces of the endplates of the upper and lower vertebral bodies.

17. A method of inserting an expandable spinal implant into a disc space between two adjacent vertebral bodies using an insertion instrument, the method comprising:
providing an expandable spinal implant having a body portion, a carriage portion, a deployment portion, and an expandable portion, the carriage portion being moveable relative to an interior cavity of the body portion from a retracted position to an extended position, the carriage portion supporting the expandable portion, the expandable portion including an upper portion and a lower portion, the upper portion being pivotally engaged to the carriage portion, and the lower portion being pivotally engaged to the carriage portion, the deployment portion being attached to the carriage portion and the expandable portion, the deployment portion being moveable between at least a first position and a second position to facilitate movement of the expandable portion between a closed position and an open position;
providing an insertion instrument having a pusher tool and a driver tool, at least a portion of the driver tool being received with the pusher tool, the pusher tool being engageable to the expandable spinal implant to move the carriage portion from the retracted position to the extended position, and the driver tool being engageable to the expandable spinal implant to move the expandable portion from the closed position to the open position;
releasably engaging the insertion instrument to the expandable spinal implant;
inserting the expandable spinal implant into the disc space between the two adjacent vertebral bodies using the insertion instrument,
actuating the pusher tool to move the carriage portion from the retracted position to the extended position; and
actuating the driver tool to move the deployment portion from the first position to the second position to move the expandable portion from the closed position to the open position.

18. The method of claim 17, wherein the upper portion includes at least one peg and the lower portion includes at least one peg, and the carriage portion includes a first indentation for receiving the at least one peg of the upper portion and the carriage portion includes a second indentation for receiving the at least one peg of the lower portion, the interaction of the at least one peg of the upper portion in the first indentation creates a first pivot point for pivoting the upper portion due to actuation of the driver tool, and the interaction of the at least one peg of the lower portion in the second indentation creates a second pivot point for pivoting the lower portion due to actuation of the driver tool.

19. The method of claim 17, wherein the deployment portion includes a deployment screw and a yoke portion engaging the deployment screw, at least a portion of the deployment screw being received in a threaded aperture of the carriage portion, and the yoke portion including an aperture therein for receiving a pin therethrough to attach the yoke portion to the upper portion, the lower portion, and the carriage portion, the deployment screw being moveable between the first position and the second position via rotation thereof with respect to the threaded aperture of the carriage portion, rotational movement of the deployment screw serving to move the yoke portion and the pin received therethrough along at least one slot of the carriage portion, and movement of the pin in the at least one slot serves to move the upper portion and the lower portion between the closed position and the open position.

20. The method of claim 17, wherein the insertion instrument includes a first sleeve portion and a second sleeve portion, the second sleeve portion being partially received in the first sleeve portion, and the pusher tool being partially received in the second sleeve portion, the first sleeve portion including a first end and a second end opposite from one another, the second sleeve portion including a first end and a second end opposite from one another, the second sleeve portion including a first arm section and a second arm section adjacent the first end thereof, the first arm section and the second arm section being biased away from one another, and wherein, when the second sleeve portion is received in the first sleeve portion, movement of the first end of the first sleeve toward the first end of the second sleeve portion serves to push the first arm portion and the second arm portion toward one another to facilitate releasable engagement of the expandable spinal implant to the insertion instrument.

* * * * *

UNITED STATES PATENT AND TRADEMARK OFFICE
CERTIFICATE OF CORRECTION

| | |
|---|---|
| PATENT NO. | : 10,076,421 B2 |
| APPLICATION NO. | : 15/824253 |
| DATED | : September 18, 2018 |
| INVENTOR(S) | : Dewey |

It is certified that error appears in the above-identified patent and that said Letters Patent is hereby corrected as shown below:

On the Title Page

Column 1, under "Related U.S. Application Data", Line 2, delete "2016." and insert -- 2016, now Pat. No. 9,937,054. --, therefor.

In the Specification

In Column 1, Line 5, delete "2016;" and insert -- 2016, now Pat. No. 9,937,054; --, therefor.

In Column 4, Line 55, delete "after the moving the" and insert -- after moving the --, therefor.

In Column 5, Line 30, delete "anther." and insert -- another. --, therefor.

In Column 8, Line 29, delete "upper jaw portion 82" and insert -- lower jaw portion 82 --, therefor.

In Column 10, Line 56, delete "its contemplated" and insert -- it's contemplated --, therefor.

In the Claims

In Column 13, Line 66, in Claim 10, delete "a end," and insert -- a first end, --, therefor.

In Column 16, Line 10, in Claim 17, delete "instrument," and insert -- instrument; --, therefor.

Signed and Sealed this
Eighth Day of January, 2019

Andrei Iancu
*Director of the United States Patent and Trademark Office*